United States Patent [19]

Tokutake et al.

[11] Patent Number: 5,302,514
[45] Date of Patent: Apr. 12, 1994

[54] MALTOOLIGOSIDE DERIVATIVE, REAGENT FOR DETERMINING α-AMYLASE ACTIVITY CONTAINING THE SAME AS EFFECTIVE INGREDIENT AND A PROCESS FOR DETERMINING THE α-AMYLASE ACTIVITY USING SAME

[75] Inventors: Shoichi Tokutake; Tadashi Tomikura, both of Noda; Kazuo Kotani; Kazunori Saito, both of Tokyo; Kohichiro Tobe, Noda, all of Japan

[73] Assignees: Kikkoman Corporation, Noda; Daiichi Pure Chemicals Co. Ltd., Tokyo; Seishin Pharmaceutical Co., Ltd., Noda, all of Japan

[21] Appl. No.: 894,468

[22] Filed: Jun. 5, 1992

[30] Foreign Application Priority Data

Jun. 26, 1991 [JP] Japan .................. 3-180473

[51] Int. Cl.$^5$ .............................. C12Q 1/40
[52] U.S. Cl. .................... 435/22; 536/4.1; 536/17.3; 536/17.5; 536/17.7; 536/18.4; 536/18.7; 536/123.13; 435/96; 435/98; 435/99
[58] Field of Search ............ 536/4.1, 17.3, 17.5, 536/17.7, 18.4, 18.7, 123.13; 435/22, 96, 98, 99

[56] References Cited

U.S. PATENT DOCUMENTS

| | | | |
|---|---|---|---|
| 4,145,527 | 3/1979 | Burns et al. | 536/17.8 |
| 4,225,672 | 9/1980 | Hall | 435/74 |
| 4,794,078 | 12/1988 | Blair | 435/22 |
| 4,812,398 | 3/1989 | Kondo et al. | 435/22 |
| 4,857,640 | 8/1989 | Henkel et al. | 536/17.7 |
| 4,945,043 | 7/1990 | Gerber | 435/70.21 |
| 4,963,479 | 10/1990 | Chavez et al. | 536/18.1 |
| 4,987,067 | 1/1991 | Ishimaru et al. | 536/18.1 |
| 5,158,872 | 10/1992 | Chavez et al. | 435/22 |
| 5,192,666 | 3/1993 | Ikenaka et al. | 536/18.6 |
| 5,208,151 | 5/1993 | Usui et al. | 536/18.5 |

FOREIGN PATENT DOCUMENTS 0252525  7/1987  European Pat. Off. .

OTHER PUBLICATIONS

"Chemical Modification of the Nonreducing, Terminal Group of Maltotriose", Ken'Ichi Takeo, Toshinari Matsunami, and Takashi Kuge, Carbohydrate Research, vol. 51 (1976), pp. 73–84.

*Primary Examiner*—Ronald W. Griffin
*Attorney, Agent, or Firm*—Banner, Birch, McKie and Beckett

[57] ABSTRACT

The present invention provides a maltooligoside derivative represented by the formula:

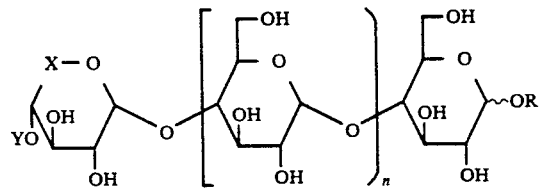

wherein n denotes an integer 3–5, R represents an aromatic chromophoric group, X represents a group >CHCH$_2$N$_3$ or >C=CH$_2$, and Y represents a hydrogen atom, a substituted or unsubstituted hydrocarbon group or an alkyl- or arylsulfonyl group, a reagent for determining α-amylase activity which comprises said maltooligoside derivative as an effective ingredient, and a process for determining α-amylase activity, characterized in that said maltooligoside derivative and coupled enzymes are added to an α-amylase containing sample to conduct an enzymatic reaction and a liberated aromatic chromophoric compound is quantitatively determined. The compound of the present invention is very useful as a substrate for determining α-amylase activity, and α-amylase activity can be easily measured accurately in a short time by using the reagent without affection of the other ingredients contained in the sample.

7 Claims, 2 Drawing Sheets

MALTOOLIGOSIDE DERIVATIVE, REAGENT FOR DETERMINING α-AMYLASE ACTIVITY CONTAINING THE SAME AS EFFECTIVE INGREDIENT AND A PROCESS FOR DETERMINING THE α-AMYLASE ACTIVITY USING SAME

BACKGROUND OF THE INVENTION (1) Field of the Invention

The present invention relates to a novel maltooligoside derivative, a reagent for determing α-amylase activity containing the derivative as an effective ingredient and a process for determining efficiently and accurately the α-amylase activity by the use of the derivative.

(2) Description of the Prior Art

Hitherto, the determination of α-amylase activity in body fluids such as serum, urine, pancreatic juice and saliva has been very important for clinical diagnoses and is an essential item in the diagnosis of acute or chronic diseases such as hepatitis, pancreatitis, pancreatic carcinoma and epidemic parotiditis.

A variety of methods have hitherto been known as for the method for determining the α-amylase activity. Among them, a method comprising utilizing as a substrate a compound [having a property of resistance (stability) to hydrolysis by a coupled enzyme] in which a non-reducing end glucose of substituted phenyl maltooligosides is modified by a variety of substituents has been widely used, recently. Said method is one that the compound is cleaved by α-amylase and the cleavage product is treated with the coupled enzyme, followed by quantitative, colorimetric determination of the resulting substituted phenols directly or, if necessary, after the adjustment of pH, or after the condensation of the phenols.

The substrate used in the aforementioned application is generally required to have the properties that only a single D-glucosidic linkage of the substrate is hydrolyzed, the pattern of action in the hydrolysis and the reaction rate do not vary depending on two α-amylases (isozymes), the hydrolyzed products are not further hydrolyzed by α-amylase, the substrate has a high affinity to α-amylase (that is, a small Km value) and a high hydrolysis rate, and that the substrate has an excellent solubility in water. However, no substrate having a modified non-reducing end which satisfies completely the requirements has hitherto been discovered.

The objects of the present invention are to overcome such defects of conventional reagents for determining the activity of α-amylase and determining methods using these reagents, and to provide a novel compound suitable as a reagnet permitting efficient and accurate determination of α-amylase activity and a novel process for determining α-amylase activity by using the compound as a reagent.

The present inventors have carried out earnest researches for the purpose of accomplishing the aforementioned objects. As a result, they have found that a specified novel maltooligoside derivative is very suitable as a reagent for determining α-amylase activity and that the aforementioned objects can be achieved by determining α-amylase activity by the use of the reagent.

SUMMARY OF THE INVENTION

That is, the present invention provides a maltooligoside derivative, represented by the formula:

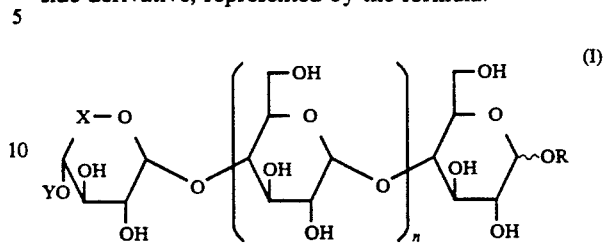

wherein n denotes an integer of 3–5, R represents an aromatic chromophoric group, X represents >CHCH$_2$N$_3$ or >C=CH$_2$, Y represents a hydrogen atom, a substituted or unsubstituted hydrocarbon group or an alkyl- or arylsulfonyl group, a reagent for determining α-amylase activity which contains the compound represented by the formula (I) as an effective ingredient, a process for determining α-amylase activity comprising adding an α-anomer of the compound having the formula (I) and α-glucosidase or glucoamylase, or mixture thereof to an α-amylase containing sample to conduct enzymatic reaction, and determining quantitatively a liberated aromatic chromophoric compound and a process for determining α-amylase activity comprising adding a β-anomer of the compound represented by the formula (I) or a mixture of the α-anomer and the β-anomer thereof, α-glucosidase and/or glucoamylase and β-glucosidase to an α-amylase containing sample to conduct enzymatic reaction and determining quantitatively a liberated aromatic chromophoric compound.

As the maltooligosaccharide portion of the maltooligoside derivative represented by the formula (I) of the present invention, all of those which correspond to saccharides ranging from α- and β-D-maltopentaose to α- and β-D-altoheptaose may be used.

X in the formula (I) represents >CHCH$_2$N$_3$ or >C=CH$_2$, and H of CH in >CHCH$_2$N$_3$ has a conformation of bonding downwards to the plane.

On the other hand, Y represents a hydrogen atom, a substituted or unsubstituted hydrocarbon group or an alkyl- or arylsulfonyl group. As the substituted or unsubstituted hydrocarbon group, there can be mentioned linear, branched or cyclic alkyl groups such as methyl, ethyl, isopropyl, butyl or cyclohexyl, aralkyl groups such as benzyl, and aryl groups such as phenyl, toluyl and naphthyl. These alkyl, aralkyl and aryl groups may be substituted by functional groups such as acyl, alkyloxy, carboxyl, nitro, halogeno, alkylsilyl and sulfonyl, and the alkyl groups may be unsaturated ones such as vinyl and allyl.

As the aforementioned alkyl- or arylsulfonyl group, there are mentioned, for example, a mesyl group, a tosyl group or a quinolinesulfonyl group.

Furthermore, as the aromatic chromophoric group R substituted on the hydroxyl group at the 1-position of the reducing end glucose in the maltooligoside derivatives represented by the formula (I), any groups which can be optically detected may be used. For example, there are mentioned the groups represented by the formulae:

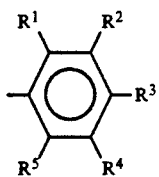

wherein R¹-R⁵, which may be the same or different, represent a hydrogen atom, a halogen atom, a nitro group, an alkyl group, an aryl group, an aralkyl group, an amino group, a sulfonic acid group or a carboxyl group, or R¹ and R² or R² and R³ may be bonded together to form a fused aromatic ring,

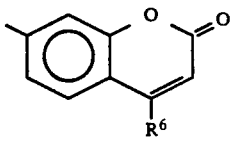

wherein R⁶ represents a hydrogen atom or an alkyl group,

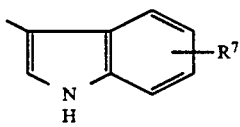

wherein R⁷ represents a hydrogen or a halogen atom, and

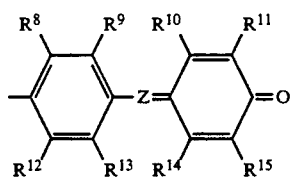

wherein R⁸-R¹⁵, which may be the same or different, represent a hydrogen atom, a halogen atom, a nitro group, an alkyl group, an aryl group, an aralkyl group, an amino group, a sulfonic acid group or a carboxyl group, R⁸ and R⁹ or R¹⁰ and R¹¹ may be bonded together to form a fused aromatic ring, R⁹ and R¹⁰ and/or R¹³ and R¹⁴ may represent a common oxygen atom, respectively, to form a fused ether ring, and Z represents a nitrogen atom or N→O.

Furthermore, the moltooligoside derivative of the formula (I) may be either the α-anomer (α-glycoside) or the β-anomer (β-glycoside).

The compound represented by the aforementioned formula (I) includes, for example, 2-chloro-4-nitrophenyl 6⁵-azido-6⁵-deoxy-β-D-maltopentaoside, 2-chloro-4-nitrophenyl 6⁵-azido-6⁵-deoxy-4⁵-O-mesyl-β-D-maltopentaoside, 2-chloro-4-nitrophenyl 5⁵-eno-β-D-maltopentaoside, 2-chloro-4-nitrophenyl 5⁵-eno- 4⁵-O-mesyl-β-D-maltopentaoside, 4-nitrophenyl 5⁷-eno-4⁷-O-methoxymethyl-α-D-maltopentaoside, 4-nitrophenyl 6⁷-azido-6⁷-deoxy-α-D-maltoheptaoside, 2,4-dichlorophenyl 6⁷-azido-6⁷-deoxy-4⁷-O-tosyl-β-D-maltoheptaoside, phenolindo-3'-chlorophenyl 6⁵-azido-6⁵-deoxy-4⁵-O-methyl-β-D-maltopentaoside, 4-methylumbelliferonyl 6⁵-azido-6⁵-deoxy-β-D-maltopentaoside, resazurinyl 5⁶-eno-α-D-maltohexaoside, luciferinyl 6⁷-azido-6⁷-deoxy-4⁷-O-allyl-β-D-maltoheptaoside, or phenolindo-3'-chlorophenyl 5⁵-eno-4⁵-O-(2-methoxy)ethoxymethyl-β-D-maltopentaoside.

In this connection, the aforementioned signals such as 6⁵-, 6⁷-, 4⁵- and 4⁷- mean that the hydroxyl groups at the 6-position and 4-position of the fifth and seventh glucoses (i.e. glucoses unit of a non-reducing end) from the reducing end side of the glucose units constituting the maltooligosaccharide are substituted.

Hitherto, in the study on the chemical modification at the non-reducing end of a maltotriose, 1,6-anhydro-6''-azido-6''-deoxy-β-maltotriose octaacetate has been known as an intermediate of the modified maltotriose ["Carbohydrate Research", 51, 73-84 (1976)]. This compound corresponds to the compound of the formula (I) wherein n equals to 1, but it is different in that the known compound has an intramolecular ethereal structure, no chromophores, and is acetyl derivative. Moreover, the compound of the formula (I) wherein n equals to 1 is hardly affected by α-amylase and thus is not suitable for a substrate for determining the α-amylase activity, so that it cannot be used for the object of the present invention.

The maltooligoside derivative represented by the formula (I) according to the present invention is a novel compound that has been described in no literatures, and any production methods thereof can be employed without special limitation.

That is, a D-maltooligoside represented by the formula:

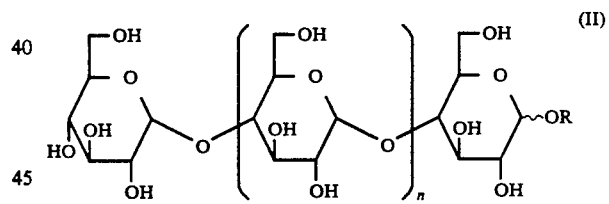

wherein R and n have the same meanings as above, which is commercially available or can be obtained by a well-known production method such as 2-chloro-4-nitrophenyl β-D-maltopentaoside, 4-nitrophenyl α-D-maltoheptaoside and phenolindo-3'-chlorophenyl β-D-maltopentaoside is used as a starting material, and a carbonyl compound represented by the formula:

wherein R¹⁶ represents a hydrogen atom, a methoxy group, an ethoxy group, an alkyl group or an aryl group, and R¹⁷ represents a methoxy group or an ethoxy group, or an acetal or a ketal thereof is reacted with the D-maltooligoside to give a 4,6-O-alkoxymethylidenized maltooligoside derivative represented by the formula:

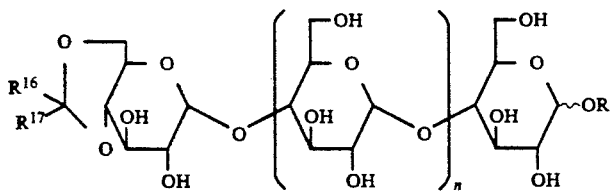

(IV)

wherein $R^{16}$ and $R^{17}$, R and n have the same meanings as defined above, such as 2-chloro-4-nitrophenyl $4^5,6^5$-O-dimethoxymethylidene-$\beta$-D-maltopentaoside, 4-nitrophenyl $4^7,6^7$-O-(1-methoxy)ethylidene-$\alpha$-D-maltoheptaoside and phenolindo-3'-chlorophenyl $4^5,6^5$-O-(1-ethoxy)ethylidene-$\beta$-D-maltopentaoside.

As the carbonyl compound represented by the formula (III) or the acetal or ketal thereof, there are mentioned, for example, tetramethoxymethane, triethyl orthoacetate or trimethyl orthoacetate.

The reaction for preparing the 4,6-O-alkoxymethylidenized maltooligoside derivative represented by the formula (IV) is generally carried out in an aprotic polar solvent such as N,N-dimethylformamide (DMF), N,N-dimethylacetamide (DMA), dimethylsulfoxide (DMSO) or hexamethylphosphoric triamide (HMPA) in the presence of a catalyst such as p-toluenesulfonic acid, hydrogen chloride, sulfuric acid, anhydrous zinc chloride and a strong acidic ion exchange resin.

The 4,6-O-alkoxymethylidenized maltooligoside derivative represented by the formula (IV) thus obtained is acylated and led to a 4,6-O-alkoxymethylidenized acylmaltooligoside derivative such as 2-chloro-4-nitrophenyl tetradeca-O-acetyl-$4^5,6^5$-O-dimethoxymethylidene-$\beta$-D-maltopentaoside, 4-nitrophenyl eicosa-O-benzoyl-$4^7,6^7$-O-(1-methoxy)ethyliden-$\alpha$-D-maltoheptaoside and phenolindo-3'-chlorophenyl tetradeca-O-butyryl-$4^5,6^5$-O-(1-ethoxy)ethylidene-$\beta$-D-maltopentaoside. In this case, as the acylating agent, carboxylic acid such as acetic acid, monochloroacetic acid, propionic acid, n-butyric acid and benzoic acid, or reactive derivatives such as acid anhydrides, acid chlorides and esters thereof are used. The condition of the acylation is not critical, and conditions conventionally used in acylation can be used.

The 4,6-O-alkoxymethylidenized acylmaltooligoside derivative thus obtained is next subjected to dealkoxymethylidenization to prepare a partially acylated maltooligoside derivative represented by the formula:

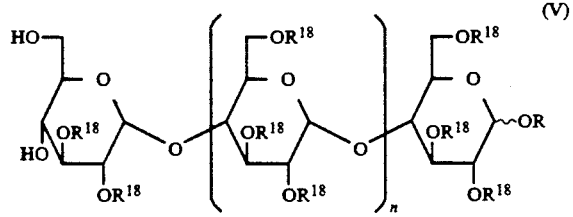

(V)

wherein $R^{18}$ represents an acyl group, and R and n have the same meanings as defined above, such as 2-chloro-4-nitrophenyl O-(2,3-di-O-acetyl-$\alpha$-D-glucopyranosyl)-(1→4)-tris[O-(2,3,6-tri-O-acetyl-$\alpha$-D-glucopyranosyl)-(1→4)]-2,3,6-tri-O-acetyl-$\beta$-D-glucopyranoside and 4-nitrophenyl O-(2,3-di-O-benzoyl-$\alpha$-D-glucopyranosyl)-(1→4)-pentakis[O-(2,3,6-tri-O-benzoyl-$\alpha$-D-glucopyranosyl)-(1→4)]-2,3,6-tri-O-benzoyl-$\alpha$-D-glucopyranoside. The condition of the aforementioned dealkoxymethylidenization is not critical, and the reaction can be conducted with a well-known method such as the one wherein acetic acid and formic acid is reacted with the 4,6-alkoxymethylidenized acylmaltooligoside derivative [see, for example, J. Am. Chem. Soc., 84, 430 (1962)].

The partially acylated maltooligoside derivative represented by the formula (V) thus obtained is next reacted with a bulky alkyl- or arylsulfonyl chloride such as tosyl chloride and naphthalenesulfonyl chloride to effect alkyl- or arylsulfonylation only the hydroxyl group at the 6-position, and then the hydroxyl group at the 4-position is modified to prepare the acylsulfonylmaltooligoside derivative represented by the formula:

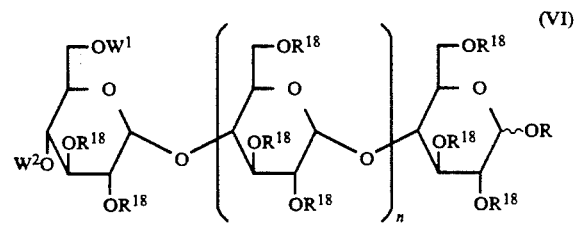

(VI)

wherein n, R and $R^{18}$ have the same meanings as defined above, $W^1$ represents an alkyl- or arylsulfonyl group, and $W^2$ represents an acyl group, a substituted or unsubstituted hydrocarbon group or an alkyl- or arylsulfonyl group, such as 2-chloro-4-nitrophenyl pentadeca-O-acetyl-$6^5$-O-tosyl-$\beta$-D-maltopentaoside, 4-nitrophenyl tetradeca-O-butyryl-$4^5$-O-acetyl-$6^5$-O-naphthalenesulfonyl-$\alpha$-D-maltopentaoside, 2-chloro-4-nitrophenyl eicosa-O-benzoyl-$4^7$-O-mesyl-$6^7$-O-tosyl-$\beta$-maltoheptaoside, and phenolindo-3'-chlorophenyl tetradeca-O-chloroacetyl-$6^5$-O-(2,4-dimethyl)benzenesulfonyl-$4^5$-O-methyl-$\beta$-D-maltopentaoside.

The condition of the alkyl- or arylsulfonylation (introduction of $W^1$) of the aforementioned hydroxyl group at the 6-position is not critical, and the reaction is usually carried out by treating the partially acylated maltooligoside derivative with 3–30 mol eq. of bulky alkyl- or arylsulfonyl halide without heating in pyridine or in a non-polar solvent such as dichloromethane and toluene in the presence of a base such as triethylamine and diazabicycloundecene (DBU).

Furthermore, in order to introduce the substituent $W^2$ to the hydroxyl group at the 4-position, acylation is carried out in the case where Y represents a hydrogen atom in the formula (I), and the introduction of a hydrocarbon group, for example alkylation or aralkylation or alkyl- or arylsulfonylation is carried out as necessary in the other cases. These reactions may be conducted, for example, in accordance with the method exemplified above in the case of acylation, in accordance with the method of treating with an alkyl halide in the presence of potassium hydroxide in DMSO in the case of alkylation [e.g. Tetrahedron, 35, 2169 (1979)], in accordance with the method of reacting with an aralkyl halide in the presence of sodium hydride in benzene in the case of aralkylation [e.g. J. Chem. Soc., 88, 82 (1966)], and in accordance with the method of reacting with sulfonyl chloride in pyridine in the case of alkyl- or arylsulfonylation [e.g. Methods of Carbohydrate Chem., 63, 99 (1978)]. When Y is an alkyl- or arylsulfonyl group, the hydroxyl groups at the 4- and 6-positions may be simultaneously sulfonylated, for example, by extending the reaction time or raising the reaction temperature or with use of a non-bulky alkyl- or arylsulfonylating agent such as methanesulfonyl chloride.

When X represents the group >CHCH$_2$N$_3$, the acylsulfonylmaltooligoside derivative obtained as above and represented by the formula (VI) is treated with sodium iodide or sodium bromide to form a 6-iodo or 6-bromo derivative, followed by reacting with, for example, sodium azide to prepare the acylazidomaltooligoside derivative of the formula:

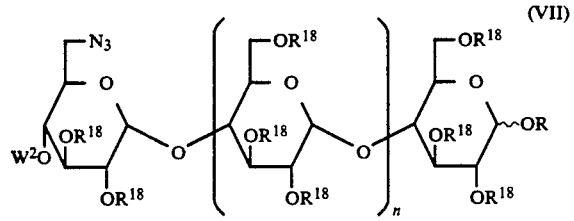

(VII)

wherein n, R, R$^{18}$ and W$^2$ have the same meanings as defined above, for example, 2-chloro-4-nitrophenyl pentadeca-O-aceyl-6$^5$-azido-6$^5$-deoxy-$\beta$-D-maltopentaoside, 4-nitrophenyl tetradeca-O-butyryl-4$^5$-O-acetyl-6$^5$-azido-6$^5$-deoxy-$\alpha$-D-maltopentaoside, 2-chloro-4-nitrophenyl eicosa-O-benzoyl-6$^7$-azido-6$^7$-deoxy-4$^7$-O-mesyl-$\beta$-D-maltopentaoside or phenolindo-3'-chlorophenyl tetradeca-o-chloroacetyl-6$^5$-azido-6$^5$-deoxy-4$^5$-O-methyl-$\beta$-D-maltopentaoside.

The condition for the iodination, bromination or azidization of the hydroxyl group at the 6-position is not critical, and the reaction is usually carried out by heating the aforementioned acylsulfonylmaltooligoside derivative to a temperature ordinarily employed in an aprotic polar solvent such as DMSO, DMF, HMPA and methyl ethyl ketone and treating with 5–50 mol eq. of sodium iodide, sodium bromide or sodium azide. In this connection, stepwise reactions of the iodination or bromination followed by the azidization after the 6-iodo or 6-bromo derivative has been obtained are not required, and the reactions may be carried out continuously in the same reaction system. The 6-bromo derivative can also be prepared by treating the aforementioned 4,6-O-alkoxymethylidenized acylmaltooligoside derivative with NBS. In this case, W$^2$ represents an acyl group.

When X represents the group >C=CH$_2$, the acylsulfonylmaltooligoside derivative thus obtained and represented by the formula (VI) is treated with sodium iodide or sodium bromide to form the 6-iodo or 6-bromo derivative, which is next treated with a dehydrohalogenation agent such as silver fluoride to prepare the acylunsaturated-maltooligoside derivative of the formula:

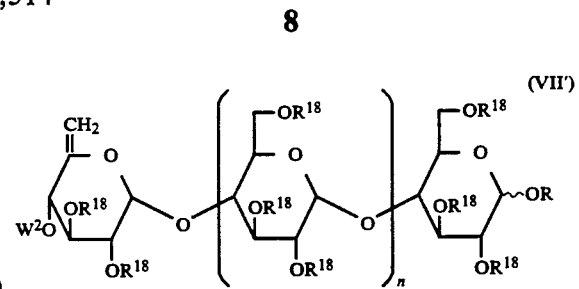

(VII')

wherein n, R, R$^{18}$ and W$^2$ have the same meanings as defined above, for example, 2-chloro-4-nitrophenyl tetradeca-O-acetyl-5$^5$-eno-4$^5$-O-mesyl-$\beta$-D-maltopentaoside, 4-nitrophenyl tetradeca-O-butyryl-4$^5$-O-acetyl-5$^5$-eno-$\alpha$-D-maltopentaoside, 2-chloro-4-nitrophenyl heneicosa-O-benzoyl- 5$^7$-eno-$\beta$-D-maltoheptaoside or phenolindo-3'-chlorophenyl tetradeca-O-chloroacetyl-5$^5$-eno-4$^5$-O-methyl-$\beta$-D-maltopentaoside.

The condition for the iodination or bromination of the hydroxyl group at the 6-position is not critical, and the reaction can be conducted, for example, by the aforementioned method. Also, the condition of the dehydrohalogenation is not critical, and the reaction is conducted by treating the aforementioned 6-iodo or 6-bromo derivative with 2–20 mol eq. of silver fluoride to a temperature ordinarily employed in pyridine or by treating with 5–50 mol eq. of base such as DBU in the aforementioned aprotic polar solvent with or without heating.

Finally, the deacylation of the acylmaltooligoside derivative represented by the formulae (VII) or (VII') gives the maltooligoside derivative represented by the formula (I) as the preferred compound, wherein Y represents a hydrogen atom when W$^2$ represents an acyl group and Y represents the same group as W$^2$ when W$^2$ represents a substituted or unsubstituted hydrocarbon group or an alkyl- or arylsulfonyl group. The condition of the deacylation is also not critical, and for example the method of treating the acylmaltooligoside derivative with a base such as potassium carbonate, aqueous ammonia and potassium cyanide in an alcohol such as methanol is employed [see "Protective Groups in Oganic Synthesis", by Theodora W. Greene, pp. 50–55, 1980, JOHN WILEY & SONS, New York].

As an alternative method for preparing the maltooligoside derivative represented by the formula (I), there is mentioned, for example, a method for preparing the aforementioned derivative by treating a 6-azido-6-deoxycyclodextrin [see, for example, Carbohyd. Res., 18, 29–37 (1971)] prepared by a well-known method with a well-known cyclodextrinase [see, for example, Japanese Patent Kokai No. 3-86701], then treating with an exo-type saccharification enzyme such as glucoamylase to give a maltooligosaccharide in which the hydroxyl group at the 6-position of the non-reducing end glucose is substituted by an azide group and introducing an aromatic chromophoric group to the maltooligosaccharide by a well-known method [see, for example, Japanese Patent Kokai No. 60-78994], or a method for preparing the aforementioned derivative by adding the aforementioned 6-azido-6-deoxycyclodextrin to a commercially available or well-known glucoside having an aromatic chromophoric group as an aglycone, treating with a well-known enzyme, cyclodextrin glucanotransferase and treating finally with an exo-type saccharification enzyme such as glucoamylase.

The maltooligoside derivative thus obtained and represented by the formula (I) is very useful for the determination of α-amylase activity, and thus the α-amylase activity can be measured with the maltooligoside derivative.

As described above, the maltooligoside derivative of the formula (I) has the α-anomer and β-anomer. When only the α-anomer is used in the measurement of the α-amylase activity, α-glucosidase or glucoamylase or both are required as the coupled enzyme system. When only the β-anomer or a mixture of the α-anomer and the β-anomer is used, β-glucosidase in addition to α-glucosidase or glucoamylase or both is required, and, if necessary, β-amylase can be also used.

As an advantaeous system for determining the α-amylase activity, there is mentioned a system of pH 4–10 which contains 0.1–10 mM of the maltooligoside derivative represented by the formula (I), 2–300 mM of a buffer, α-glucosidase and/or glucoamylase in a concentratin of 5–1000 units/ml as the coupled enzyme and β-glucosidase, when employed, in a concentration of 0.5–30 units/ml. The buffer used in the system includes, for example, phosphates, acetates, carbonates, the Good's buffer, borates, citrates or dimethylglutarates.

The α-glucosidase may be derived from any sources such as animals, vegetables and microorganisms, with the one derived from yeast being preferred. Also, glucoamylase may be derived from any sources, with the one derived from Rizopus species being preferred. Further, β-glucosidase may also be derived from any sources, and the one, for example, derived from almond's seed may be used.

The β-amylase may also be derived from any sources, and the ones, for example, derived from bacteria or vegetables may be used.

To such a system, if necessary, a variety of conventional additives such as glycerin, bovine serum albumin, α- or β-cyclodextrin and Triton X-100 may be added, in addition to the aforementioned ingredients, as a dissolution aid or a stabilizer in a range wherein the object of the present invention will not be impaired. As an α-amylase activator, $Cl^-$, $Ca^{2+}$ or $Mg^{2+}$ ions which are used in the form of NaCl, $MgCl_2$, $MgSO_4$, $CaCl_2$ or $CaCl_2.H_2O$ may be also added. These additives may be used alone or in combination of the two or more during appropriate steps of preparing the aforementioned system.

The reagent of the present invention may be used in the form of a dry product or a solution or in the form of a film carrier such as sheet and impregnating paper into which the reagent has been impregnated. By using the reagent of the present invention, the activity of α-amylase contained in a variety of samples can be determined accurately and at a high sensitivity with an easy procedure.

DESCRIPTION OF THE PREFERRED EMBODIMENTS

Figure 1:
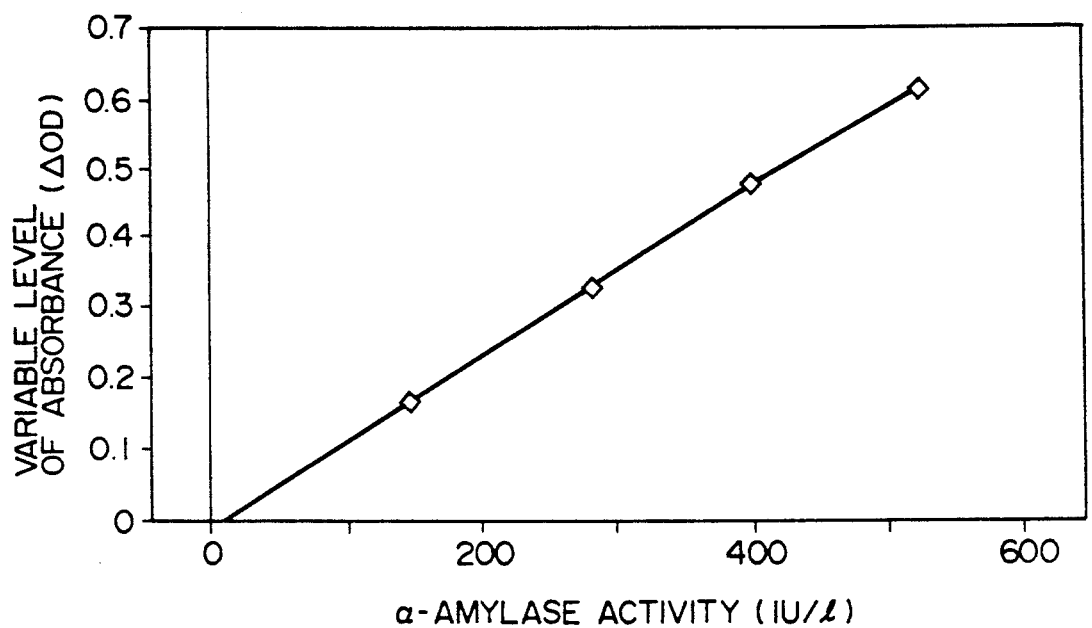
FIG. 1 is a graph which shows a calibration curve used for determining the activity of α-amylase in Example 5.

The process of the present invention is now explained with reference to preferred embodiments.

First, 5–1000 units/ml, preferably 10–500 units/ml of α-glucosidase or glucoamylase or both as the coupled enzyme are added to a sample containing α-amylase. When the maltooligoside derivative of the formula (I) contains the β-anomer, 0.5–30 units/ml, preferably 1–15 units/ml of β-glucosidase is further added, and simultaneously or thereafter, 0.1–10 mM, preferably 0.3–5 mM of the maltooligoside derivative is added together with the buffer. The mixture is subsequently subjected to enzyme reaction under the condition at a temperature of 25°–45° C., preferably 35°–40° C. and pH of 4–10, preferably 6–8 for at least 1 minute, preferably for 2–10 minutes. The variation of the absorbance of the resulting aromatic chromophoric compound, directly or after the adjustment of pH or the condensation in a usual way, is measured continuously or intermittently at an appropriate wavelength, and the activity of α-amylase in the sample is calculated by comparing the aforementioned of the absorbance with that of a standard α-amylase sample previously determined. The activity of α-amylase may also be calculated from the absorptivity coefficient of the aromatic chromophoric compound.

Although the α-amylase containing sample used in the present invention may be the one which has the α-amylase activity and is not critical, culture liquids of microorganisms, extracts of vegetables, or body fluids or tissues of animals and extracts thereof may be specifically used. When the α-amylase containing sample is solid, it is preferably dissolved or suspended once in purified water or a buffer as described above. Alternatively, insolubles may be removed by such operations as filtration.

The maltooligoside derivative represented by the formula (I) according to the present invention is a novel compound which satisfies all of the requirements as a substrate and is very useful as a reagent for determining the activity of α-amylase. By using the aforementioned derivative, the α-amylase activity may be measured accurately and easily in a short period by an automatic analytical method or a manual method without any influence of glucose, maltose, bilirubin or hemoglobin present in the sample.

The compound of the present invention is stable over a long period and has a further advantage of increasing the utility as the substrate.

EXAMPLE

The present invention is further described in detail with reference to examples, which should not be construed as limiting the scope of the invention.

In respective example, the wavelength of a maximum absorbance was measured in methanol unless otherwise specified, and optical rotation was measured with the D-ray at 25° C.

EXAMPLE 1

Preparation of 2-chloro-4-nitrophenyl $5^5$-eno-$4^5$-O-mesyl-$\beta$-D-maltopentaoside (1) Preparation of 2-chloro-4-nitrophenyl $4^5,6^5$-O-dimethoxymethylidene-$\beta$-D-maltopentaoside A commercially available 2-chloro-4-nitrophenyl $\beta$-D-maltopentaoside in an amount of 15.0 g (15.2 mmol) was dissolved in 75 ml of anhydrous DMF, and 15.0 ml (113 mmol) of tetramethoxymethane and 7.5 g of Amberlyst (15E)$^{Trade\ Mark}$ manufactured by Japan ORGANO Company were further added. The mixture was subjected to reaction with stirring at 35° C. for 4 hours. Next, the reaction mixture was slowly added dropwise to 2.0 l of a 100 mM phosphate buffer (pH=7.0) under ice-cooling with stirring. The resulting mixture was purified by ODS (octadecylsilica gel) column chromatography, and the objective fraction eluted with an acetonitrile-water mixed solution (3:7 by volume) was concentrated and recrystallized from isopropanol-methanol to give 10.7 g of 2-chloro-4-nitrophenyl $4^5,6^5$-O-dimethoxymethylidene-$\beta$-D-maltopentaoside (10.1 mmol, yield 66.5%).

Melting point (°C.): 93.0–95.0 (with decomposition).

UV-visible absorption spectrum: absorptionn maximum wavelength [$\lambda$max] (nm)=295 (log $\epsilon$=3.95), 227 (sh), (log $\epsilon$=4.17).

IR spectrum (cm$^{-1}$): 3420, 2940, 1648, 1588, 1524, 1490, 1352, 1276, 1246, 1154, 1082, 1050, 1026, 930, 898.

NMR spectrum (200 MHz) ppm (DMSO-d$_6$) 3.25–3.85 (m), 3.23 (3H, s), 3.30 (3H, s), 3.89 (1H, d, J=3.9 Hz), 4.30–4.70 (m), 5.04 (2H, d, J=3.2 Hz), 5.10 (1H, d, J=3.7 Hz), 5.12 (1H, d, J=3.4 Hz), 5.27 (1H, d, J=7.6 Hz), 5.25–5.70 (m), 7.47 (1H, d, J=9.3 Hz), 8.19 (1H, dd, J=9.3 Hz, 2.7 Hz), 8.31 (1H, d, J=2.7 Hz).

High performance liquid chromatography [manufactured by Nacalai Tesque Inc., COSMOSIL C$_{18}$ column (4.6 mm ID×250 mm), UV$_{280}$ nm detection, eluent: acetonitrile/water=1:4 (v/v), flow rate: 1.0 ml/min]: t$_R$=10.2 min.

Optical rotation [$\alpha$]: (c 0.50, 50 mM phosphate buffer): +86.7°.

| Elemental analysis for C$_{39}$H$_{58}$ClNO$_{30}$: | | | |
|---|---|---|---|
| | C | H | N |
| Calculated (%): | 44.35 | 5.53 | 1.33 |
| Found (%): | 44.55 | 5.43 | 1.34 |

(2) Preparation of 2-chloro-4-nitrophenyl O-(2,3-di-O-acetyl-$\alpha$-D-glucopyranosyl)-(1→4)-tris[O-(2,3,6-tri-O-acetyl-$\alpha$-D-glucopyranosyl)-(1→4)]-2,3,6-tri-O-acetyl-$\beta$-D-glucopyranoside 2-chloro-4-nitropheny $4^5,6^5$-O-dimethoxymethylidene-$\beta$-D-maltopentaoside (3.00 g, 2.84 mmol) obtained in the step (1) of Example 1 was dissolved in 60 ml of pyridine. Acetic anhydride (30 ml, 384 mmol) was added to the solution and the mixture was subjected to reaction with stirring at room temperature for 2 days. The reaction mixture was then concentrated under reduced pressure to remove pyridine, acetic anhydride and acetic acid. The obtained oily acetyl derivative was dissolved in 100 ml of acetic acid without purification, 25 ml of water was added to the solution, and the mixture was reacted with stirring at 30° C. for 3 days. The reaction mixture was slowly dropped in 600 ml of ice-water with stirring, and the mixture was extracted thrice with 600 ml of dichloromethane. The dichloromethane layer was washed thrice with 600 ml of water and dried over anhydrous sodium sulfate. After filtration, the filtrate was concentrated under reduced pressure to remove dichloromethane. The residue was purified by silica gel column chromatography, and the objective fraction eluted with an ethyl acetate-methanol-dichloromethane mixed solution (66:2.5:33 by volume) was concentrated to give 2.08 g of 2-chloro-4-nitrophenyl O-(2,3-di-O-acetyl-$\alpha$-D-glucopyranosyl)-(1→4)-tris-[O-(2,3,6-tri-o-acetyl-$\alpha$-D-glucopyranosyl)-(1→4)]-2,3,6-tri-O-acetyl-$\beta$-D-glucopyranoside (1.32 mmol, two-step total yield 46.5%).

Melting point (°C.): 126.0–130.0.

UV-visible absorption spectrum: absorption maximum wavelength [$\lambda$max (CH$_3$CN)] (nm)=282 (log $\epsilon$=3.94).

IR spectrum (cm$^{-1}$): 3480, 2970, 1752, 1588, 1530, 1486, 1432, 1372, 1350, 1236, 1030, 944, 898.

NMR spectrum (200 MHz) ppm (CDCl$_3$) 1.81–2.12 (ca. 40H, each s), 3.50–4.74 (m), 5.05 (m), 7.22 (1H, d, J=9.0 Hz), 8.09 (1H, dd, J=9.0 Hz, 2.7 Hz), 8.22 (1H, d, J=2.7 Hz).

High performance liquid chromatography [manufactured by Nacalai Tesque Inc., COSMOSIL C$_{18}$ column (4.6 mm ID×150 mm), UV$_{280}$ nm detection, eluent: acetonitrile/water=7:3 (v/v), flow rate: 1.0 ml/min]: t$_R$=4.2 min.

Optical rotation[$\alpha$]: (c 0.25, 1,4-dioxane): +88.0°.

(3) Preparation of 2-chloro-4-nitrophenyl O-(2,3-di O-acetyl-4,6-di-O-mesyl-$\alpha$-D-glucopyranosyl)-(1→4)-tris[O-(2,3,6-tri-O-acetyl-$\alpha$-D-glucopyranosyl)-(1→4)]2,3,6-tri-O-acetyl-$\beta$-D-glucopyranoside 2-chloro-4-nitrophenyl O-(2,3-di-O-acetyl-$\alpha$-D-glucopyranosyl)-(1→4)-tris[O-(2,3,6-tri-O-acetyl-$\alpha$-D-glucopyranosyl)-(1→4)]-2,3,6-tri-O-acletyl-$\beta$-D-glucopyranoside (11.0 g, 7.00 mmol) obtained in the same manner as in the step (2) of Example 1 was dissolved in 500 ml of pyridine, and 4.9 ml of mesyl chloride (63.3 mmol) and 20.0 g of molecular sieves were added to the solution. The mixture was subjected to reaction with stirring at room temperature for 16 hours. The reaction mixture was next filtered through a Celite bed, and pyridine contained in the filtrate was removed by evaporation under reduced pressure. The residue was purified by silica gel column chromatography, and the objective fraction eluted with an ethyl acetate-methanol-dichloromethane mixed solution (100:1:200 by volume) is concentrated to give 11.6 g of 2-chloro-4-nitrophenyl O-(2,3-di-O-acetyl-4,6-di-O-mesyl-$\alpha$-D-glucopyranosyl)-(1→4)-tris[O-(2,3,6-tri-O-acetyl-$\alpha$-D-glucopyranosyl)-(1→4)]-2,3,6-tri-O-acetyl-$\beta$-D-glucopyranoside (6.67 mmol, yield 95.3%).

Melting point (°C.): 116.0–119.0

UV-visible absorption spectrum: absorption maximum wavelength [$\lambda$max] (nm)=283 (log $\epsilon$=3.98), 226 (sh), 209 (log $\epsilon$=4.23).

IR spectrum (cm$^{-1}$): 2950, 1752, 1586, 1528, 1368, 1350, 1238, 1176, 1032, 896, 826.

NMR spectrum (200 MHz) ppm (CDCl$_3$) 2.00–2.19 (ca. 40H, each s), 3.08 (3H, s), 3.10 (3H, s), 3.85–4.85 (m), 5.15–5.50 (m), 7.29 (1H, d, J=9.2 Hz), 8.16 (1H, dd, J=9.2 Hz, 2.7 Hz), 8.29 (1H, d, J=2.7 Hz).

High performance liquid chromatography [manufactured by Nacalai Tesque Inc., COSMOSIL C$_{18}$ column (4.6 mm ID×150 mm), UV$_{280}$ nm detection, eluent:

acetonitrile/water=3:1 (v/v), flow rate: 1.0 ml/min]: $t_R$=4.0 min.

Optical rotation [α]: (c 0.674, 1,4-dioxane): +85.8°.

| Elemental analysis for $C_{66}H_{86}ClNO_{46}S_2$: | | | |
|---|---|---|---|
| | C | H | N |
| Calculated (%): | 45.85 | 5.01 | 0.81 |
| Found (%): | 46.05 | 5.09 | 0.78 |

(4) Preparation of 2-chloro-4-nitrophenyl O-(2,3-di-O-acetyl-6-deoxy-6-iodo-4-O-mesyl-α-D-glucopyranosyl)-(1→4)-tris[O-(2,3,6-tri-O-acetyl-α-D-glucopyranosyl)-(1→4)]-2,3,6-tri-O-acetyl-β-D-glucopyranoside 2-chloro-4-nitrophenyl O-(2,3-di-O-acetyl-4,6-di-O-mesyl-α-D-glucopyranosyl)-(1→4)-tris[O-(2,3,6-tri-O-acetyl-α-D-glucopyranosyl)-(1→4)]-2,3,6-tri-O-acetyl-α-D-glucopyranoside (11.6 g, 6.67 mmol) obtained in the step (3) of Example 1 was dissolved in 1000 ml of methyl ethyl ketone, and 30.2 g of sodium iodide (201 mmol) was added to the solution. The mixture was subjected to reaction with stirring at 85° C. for 6 hours. The reaction mixture was next filtered through a Celite bed, and methyl ethyl ketone in the filtrate was removed by evaporation under reduced pressure. The residue was purified by silica gel column chromatography, and the objective fraction eluted with an ethyl acetate-methanol-dichloromethane mixed solution (100:1:200 by volume) is concentrated to give 10.3 g of 2-chloro-4-nitrophenyl O-(2,3-di-O-acetyl-6-deoxy-6-iodo-4-O-mesyl-α-D-glucopyranosyl)-(1→4)-tris[O-(2,3,6-tri-o-acetyl-α-D-glucoyranosyl)-(1→4)]-2,3,6-tri-O-acetyl-β-D-glucopyranoside (5.85 mmol, yield 87.7%).

Melting point (°C.): 127.0-129.0

UV-visible absorption spectrum: absorption maximum wavelength [λmax] (nm)=283 (log ε=3.98), 227 (sh), 209 (log ε=4.22).

IR spectrum (cm$^{-1}$): 3550, 2960, 1750, 1586, 1528, 1486, 1430, 1372, 1350, 1234, 1180, 1040, 960, 898, 828.

NMR spectrum (200 MHz) ppm (CDCl$_3$) 2.00-2.19 (ca. 40H, each s), 3.06 (3H, s), 3.30 (1H, dd, J=11.5 Hz, 5.4 Hz), 3.50 (1H, dd, J=11.5 Hz, 1.5 Hz), 3.68 (1H, ddd, J=8.8 Hz, 5.4 Hz, 1.5 Hz), 3.85-4.85 (m), 5.15-5.50 (m), 7.28 (1H, d, J=9.0 Hz), 8.16 (1H, dd, J=9.0 Hz, 2.7 Hz), 8.29 (1H, d, J=2.7 Hz).

High performance liquid chromatography [manufactured by Nacalai Tesque Inc., COSMOSIL C$_{18}$ column (4.6 mm ID×150 mm), UV$_{280}$ nm detection, eluent: acetonitrile/water=3:1 (v/v), flow rate: 1.0 ml/min]: $t_R$=5.6 min.

Optical rotation [α]: (c 0.674, 1,4-dioxane): +80.7°.

| Elemental analysis for $C_{65}H_{83}ClINO_{43}S$: | | | |
|---|---|---|---|
| | C | H | N |
| Calculated (%): | 44.34 | 4.75 | 0.80 |
| Found (%): | 44.34 | 4.82 | 0.82 |

(5) Preparation of 2-chloro-4-nitrophenyl O-(2,3-di-O-acetyl-4-O-mesyl-α-D-xylohex-5-enopyranosyl)-(1→4)-tris[O-(2,3,6-tri-O-acetyl-α-D-glucopyranosyl)-(1→4)]-2,3,6-tri-O-acetyl-β-D-glucopyranoside 2-chloro-4-nitrophenyl O-(2,3-di-O-acetyl-6-deoxy-6-iodo-4-O-mesyl-α-D-glucopyranosyl)-(1→4)-tris-[O-(2,3,6-tri-O-acetyl-α-D-glucopyranosyl)-(1→4)]-2,3,6-tri-O-acetyl-β-D-glucopyranoside (2.84 g, 1.61 mmol) obtained in the step (4) of Example 1 was dissolved in 170 ml of pyridine, and 2.05 g of silver fluoride (16.1 mmol), 28.4 mg of N,N-dimethylaminopyridine (0.232 mmol) and 5.7 g of molecular sieves were added to the solution. The mixture was subjected to reaction at a temperature of 25° C. for 15 hours with stirring. The reaction mixture was next filtered through a Celite bed, and pyridine in the filtrate was removed by evaporation under reduced pressure. The residue was purified by silica gel column chromatography, and the objective fraction eluted with an ethyl acetate-methanol-dichloromethane mixed solution (100:1:400 by volume) is concentrated to give 1.89 g of 2-chloro-4-nitrophenyl O-(2,3-di-O-acetyl-4-O-mesyl-α-D-xylohex-5-enopyranosyl)-(1→4)-tris[O-(2,3,6-tri-O-acetyl-α-D-glucopyranosyl)-( 1→4)]-2,3,6-tri-O-acetyl-β-D-glucopyranoside (1.16 mmol, yield 72.0%).

Melting point (°C.): 113.0-115.0.

UV-visible absorption spectrum: absorption maximum wavelength [λmax] (nm)=283 (log ε=3.99), 227 (sh), 209 (log ε=4.25).

IR spectrum (cm$^{-1}$): 3490, 2970, 2110, 1748, 1586, 1532, 1488, 1434, 1372, 1350, 1236, 1182, 1030, 896.

NMR spectrum (200 MHz) ppm (CDCl$_3$) 1.99-2.18 (ca. 40H, each s), 3.10 (3H, s), 3.80-4.95 (m), 5.05-5.50 (m), 7.28 (1H, d, J=9.0 Hz), 8.16 (1H, dd, J=9.0 Hz, 2.7 Hz), 8.29 (1H, d, J=2.7 Hz).

High performance liquid chromatography [manufactured by Nacalai Tesque Inc., COSMOSIL C$_{18}$ column (4.6 mm ID×150 mm), UV$_{280}$ nm detection, eluent: acetonitrile/water=3:1 (v/v), flow rate: 1.0 ml/min]: $t_R$=4.5 min.

Optical rotation [α]: (c 0.504, 1,4-dioxane): +75.3°.

| Elemental analysis for $C_{65}H_{82}ClNO_{43}S$: | | | |
|---|---|---|---|
| | C | H | N |
| Calculated (%): | 47.81 | 5.06 | 0.86 |
| Found (%): | 47.42 | 5.08 | 0.86 |

(6) Preparation of 2-chloro-4-nitrophenyl 5$^5$-eno-4$^5$-O-mesyl-β-D-maltopentaoside To 1.52 g of 2-chloro-4-nitrophenyl O-(2,3,-di-O-acetyl- 4-O-mesyl-α-D-xylohex-5-enopyranosyl)-(1→4)-tris[O-(2,3,6-tri-O-acetyl-α-D-glucopyranosyl(1→4)]-2,3,6-tri-O-acetyl-β-D-glucopyanoside (0.931 mmol) obtained in the step (5) of Example 1 were added 150 ml of methanol and 193 mg of anhydrous potassium carbonate (1.40 mmol), and the mixture was subjected to reaction at a temperature of 25° C. for 15 hours with stirring. The reaction mixture was next concentrated under reduced pressure to remove methanol contained in the mixture. The residue was purified by ODS column chromatography, and the objective fraction eluted with an acetonitrile-water mixed solution (25:75 by volume) is concentrated and lyophilized to give 746 mg of 2-chloro-4-nitrophenyl 5⁵-eno-4⁵-O-mesyl-β-D-maltopentaoside (0.715 mmol, yield 76.8%).

Melting point (°C.): 175.0–180.0 (with decomposition).

UV-visible absorption spectrum: absorption maximum wavelength [λmax] (nm)=289 (log $\epsilon$=4.01), 228 (sh), 209 (log $\epsilon$=4.43).

IR spectrum (cm$^{-1}$): 3400, 2930, 1644, 1584, 1520, 1486, 1350, 1274, 1250, 1152, 1078, 1020, 928, 890.

NMR spectrum (200 MHz) ppm (DMSO-d$_6$) 3.25–3.85 (m), 3.29 (3H, s), 4.05 (1H, br s), 4.30–4.60 (m), 4.56 (2H, d, J=2.0 Hz), 5.05 (2H, d, J=3.4 Hz), 5.11 (1H, d, J=3.7 Hz), 5.19 (1H, d, J=2.2 Hz), 5.26 (1H, d, J =7.3 Hz), 5.25–5.65 (m), 7.47 (1H, d, J=9.3 Hz), 8.18 (1H, dd, J=9.3 Hz, 2.7 Hz), 8.29 (1H, d, J=2.7 Hz).

High performance liquid chromatography [manufactured by Tosoh Corp., TSK gel Amide-80 column (4.6 mm ID×250 mm), UV$_{280}$ nm detection, eluent:

acetonitrile/water=3:1 (v/v), flow rate: 1.0 ml/min]: $t_R$=5.2 min.

Optical rotation [α]: (c 0.512, H$_2$O): +84.5°.

| Elemental analysis for C$_{37}$H$_{54}$ClNO$_{29}$S: | | | |
|---|---|---|---|
| | C | H | N |
| Calculated (%): | 42.55 | 5.21 | 1.34 |
| Found (%): | 42.23 | 5.28 | 1.40 |

EXAMPLE 2

Preparation of 2-chloro-4-nitrophenyl 6⁵-azido-6⁵-deoxy-4⁵-O-mesyl-β-D-maltopentaoside (1) Preparation of 2-chloro-4-nitrophenyl O-(2,3-di-O-acetyl-6-azido-6-deoxy-4-O-mesyl-α-D-glucopyranosyl)-(1→4)-tris[O-(2,3,6-tri-O-acetyl-α-D-glucopyranosyl)-(1→4)-2,3,6-tri-O-acetyl-β-D-glucopyranoside 2-chloro-4-nitrophenyl O-(2,3-di-O-acetyl-6-deoxy-6-iodo-4-O-mesyl-α-D-glucopyranosyl)-(1→4)-tris[O-(2,3,6-tri-O-acetyl-α-D-glucopyranosyl)-(1→4)-2,3,6-tri-O-acetyl-β-D-glucopyranoside (1.50 g, 0.852 mmol) obtained in the same operation as in the step (4) of Example 1 was dissolved in 130 ml of DMSO, and 831 mg of sodium azide (12.8 mmol) was added to the solution. The mixture was subjected to reaction with stirring at 80° C. for 3 hours. Next, 700 ml of toluene was added to the reaction mixture, and the mixture was washed thrice with each 300 ml of an aqueous 3% by weight NaCl. The toluene layer was then dried over anhydrous sodium sulfate and filtered through a cotton plug, and toluene in the filtrate was removed under reduced pressure. The residue was purified by silica gel column chromatography, and the objective fraction eluted with an ethyl acetate-methanol-dichloromethane mixed solution (100:1:400 by volume) was concentrated to give 1.27 g of 2-chloro-4-nitrophenyl O-(2,3-di-O-acetyl-6-azido-6-deoxy-4-O-mesyl-α-D-glucopyranosyl)-(1→4)-tris[O-(2,3,6-tri-O-acetyl-α-D-glucopyranosyl)-(1→4)]-2,3,6-tri-O-acetyl-β-D-glucopyranoside (0.758 mmol, yield 89.0%).

Melting point (°C.): 115.0–117.0.

UV-visible absorption spectrum: absorption maximum wavelength [λmax (CH$_3$CN)] (nm)=283 (log $\epsilon$=3.97), 227 (sh), 209 (log $\epsilon$=4.22).

IR spectrum (cm$^{-1}$): 3490, 2960, 2110, 1754, 1532, 1372, 1350, 1236, 1188, 1032, 958, 898.

NMR spectrum (200 MHz) ppm (CDCl$_3$) 2.00–2.19 (ca. 40H, each s), 3.04 (3H, s), 3.43–3.60 (2H, AB like), 3.85–4.85 (m), 5.15–5.50 (m), 7.28 (1H, d, J=9.0 Hz), 8.16 (1H, dd, J=9.0 Hz, 2.7 Hz), 8.30 (1H, d, J=2.7 Hz).

High performance liquid chromatography [manufactured by Nacalai Tesque Inc., COSMOSIL C$_{18}$ column (4.6 mm ID×250 mm), UV$_{280}$ nm detection, eluent: acetonitrile/water=3:1 (v/v), flow rate: 1.0 ml/min]: $t_R$=7.8 min.

Optical rotation [α]: (c 0.500, 1,4-dioxane): +92.6°.

| Elemental analysis for C$_{65}$H$_{83}$ClN$_4$O$_{43}$S: | | | |
|---|---|---|---|
| | C | H | N |
| Calculated (%): | 46.59 | 4.99 | 3.34 |
| Found (%): | 46.43 | 5.01 | 3.38 |

(2) Preparation of 2-chloro-4-nitrophenyl 6⁵-azido-6⁵-deoxy-4⁵-O-mesyl-β-D-maltopentaoside The procedure in the step (6) of Example 1 was repeated except that 1.22 g of 2-chloro-4-nitrophenyl O-(2,3-di-O-acetyl-6-azido-6-deoxy-4-O-mesyl-α-D-glucopyranosyl)-(1→4)-tris[O-(2,3,6-tri-O-acetyl-α-D-glucopyranosyl)-(1→4)]-2,3,6-tri-O-acetyl-β-D-glucopyranoside (0.728 mmol) obtained in the step (1) of Example 2 was employed as the starting material to give 687 mg of the desired product 2-chloro-4-nitrophenyl 6⁵-azido-6⁵-deoxy-4⁵-O-mesyl-β-D-maltopentaoside (0.632 mmol, yield 86.8%).

Melting point (°C.): 170.0–172.0 (with decomposition).

UV-visible absorption spectrum: absorption maximum wavelength [λmax] (nm)=289 (log $\epsilon$=3.96), 227 (log $\epsilon$=3.98), 209 (log $\epsilon$=4.18).

IR spectrum (cm$^{-1}$): 3400, 2930, 2110, 1632, 1584, 1522, 1486, 1350, 1276, 1250, 1172, 1152, 1080, 1026, 958, 896.

NMR spectrum (200 MHz) ppm (DMSO-d$_6$): 3.20–3.85 (m), 3.24 (3H, s), 3.85–3.95 (1H, ddd like), 4.28 (2H, br t, J=7.2 Hz), 4.40–4.60 (m), 5.05 (2H, d, J=3.2 Hz), 5.10 (1H, d, J=5.4 Hz), 5.25 (1H, d, J=3.9 Hz), 5.27 (1H, d, J=7.3 Hz), 5.30–5.70 (m), 7.47 (1H, d, J =9.3 Hz), 8.19 (1H, dd, J=9.0 Hz, 2.7 Hz), 8.31 (1H, d, J=2.7 Hz).

High performance liquid chromatography [manufactured by Tosoh Corp., TSK gel Amide-80 column (4.6 mm ID×250 mm), UV$_{280}$ nm detection, eluent: acetonitrile/water=3:1 (v/v), flow rate: 1.0 ml/min]: $t_R$=4.6 min.

Optical rotation [α]: (c 0.516, H$_2$O): +86.1°.

| Elemental analysis for C$_{37}$H$_{55}$ClN$_4$O$_{29}$S: | | | |
|---|---|---|---|
| | C | H | N |
| Calculated (%): | 40.87 | 5.10 | 5.15 |
| Found (%): | 40.62 | 4.92 | 5.05 |

EXAMPLE 3

Preparation of 2-chloro-4-nitrophenyl 6⁵-azido-6⁵-deoxy-β-D-maltopentaoside (1) Preparation of 2-chloro-4-nitrophenyl O-(2,3-di-O-acetyl-6-O-tosyl-α-D-glucopyranosyl)-(1→4)-tris-[O-(2,3,6-tri-O-acetyl-α-D-glucopyranosyl)-(1→4)-2,3,6-tri-O-acetyl-β-D-glucopyranoside 2-chloro-4-nitrophenyl O-(2,3-di-O-acetyl-α-D-glucopyranosyl)-( 1→4)-tris[O-(2,3,6-tri-O-acetyl-α-D-glucopyranosyl)-(1→4)]-2,3,6-tri-O-acetyl-β-D-glucopyranoside (11.6 g, 7.38 mmol) obtained in the same manner as in the step (2) of Example 1 was dissolved in 300 ml of pyridine, and 21.1 g (110 mmol) of tosyl chloride was added to the solution. The mixture was subjected to reaction with stirring at room temperature for 5 hours. Then, pyridine contained in the reaction mixture was removed by evaporation under reduced pressure. The residue was purified by silica gel column chromatography, and the objective fraction eluted with an ethyl acetate-methanol-dichloromethane mixed solution (50:1:100 by volume) is concentrated to give 6.43 g of 2-chloro-4-nitrophenyl O-(2,3-di-O-acetyl-6-O-tosyl-α-D-glucopyranosyl)-(1→4)-tris[O-(2,3,6-tri-O-acetyl-α-D-glucopyranosyl)-(1→4)]-2,3,6-tri-o-acetyl-β-D-glucopyranoside (3.72 mmol, yield 50.5%).

Melting point (°C.): 109.0–113.5.

UV-visible absorption spectrum: absorption maximum wavelength [λmax (CH₃CN)] (nm)=281 (log ε=3.95), 272 (sh).

IR spectrum (cm⁻¹): 3490, 2970, 1752, 1586, 1528, 1486, 1430, 1372, 1350, 1240, 1178, 1034, 942.

NMR spectrum (200 MHz) ppm (CDCl₃) 1.99–2.17 (ca. 40H, each s), 2.45 (3H, s), 3.50–4.80 (m), 5.10–5.50 (m), 7.27 (1H, d, J=9.0 Hz), 7.33 (2H, d, J=8.5 Hz), 7.79 (2H, d, J=8.5 Hz), 8.15 (1H, dd, J=9.0 Hz, 2.7 Hz), 8.29 (1H, d, J=2.7 Hz).

High performance liquid chromatography [manufactured by Nacalai Tesque Inc., COSMOSIL C₁₈ column (4.6 mm ID×150 mm), UV₂₈₀ nm detection, eluent: acetonitrile/water=7:3 (v/v), flow rate: 1.0 ml/min]: $t_R$=8.3 min.

Optical rotation [α]:(c 0.650, 1,4-dioxane): +88.0°.

| Elemental analysis for C₇₁H₈₈ClNO₄₄S: | | | |
|---|---|---|---|
| | C | H | N |
| Calculated (%): | 49.38 | 5.14 | 0.81 |
| Found (%) | 49.14 | 5.10 | 0.79 |

(2) Preparation of 2-chloro-4-nitrophenyl O-(2,3,4-tri-O-acetyl-6-O-tosyl-α-D-glucopyranosyl)-(1→4)-tris[O-(2,3,6-tri-O-acetyl-α-D-glucopyranosyl)-(1→4)]-2,3,6-tri-O-acetyl-β-D-glucopyranoside 2-chloro-4-nitrophenyl O-(2,3-di-O-acetyl-6-O-tosyl-α-D-glucopyranosyl)-(1→4)-tris[O-(2,3,6-tri-O-acetyl-α-D-glucopyranosyl)-(1→4)]-2,3,6-tri-O-acetyl-β-D-glucopyranoside (4.24 g, 2.46 mmol) obtained in the step (1) of Example 3 was dissolved in 20 ml of pyridine, and 10 ml of acetic anhydride was added to the solution. The mixture was subjected to reaction with stirring at room temperature for 15 hours. Pyridine in the reaction mixture was then removed by evaporation under reduced pressure. The residue was purified by silica gel column chromatography, and the objective fraction eluted with an ethyl acetate-methanol-dichloromethane mixed solution (40 :1:100 volume) is concentrated to give 2.90 g of 2-chloro-4-nitrophenyl O-(2,3,4-tri-O-acetyl-6-O-tosyl-α-D-glucopyranosyl)-(1→4)-tris[O-(2,3,6-tri-O-acetyl-α-D-glucopyranosyl)-(1→4)]-2,3,6-tri-O-acetyl-β-D-glucopyranoside (1.64 mmol, yield 66.6%).

Melting point (°C.): 116.5–118.0.

UV-visible absorption spectrum: absorption maximum wavelength [λmax (CH₃CN)] (nm)=284 (log ε=3.97), 226 (log ε=4.34).

IR spectrum (cm⁻¹): 3490, 2960, 1754, 1584, 1528, 1486, 1432, 1372, 1352, 1238, 1180, 1040, 994, 940, 898.

NMR spectrum (200 MHz) ppm (CDCl₃) 1.93–2.19 (ca. 40H, each s), 2.45 (3H, s), 3.80–4.80 (m), 4.96 (1H, t like), 5.10–5.50 (m), 7.28 (1H, d, J=9.0 Hz), 7.35 (2H, d, J=8.2 Hz), 7.78 (2H, d, J=8.2 Hz), 8.16 (1H, dd, J=9.0 Hz, 2.4 Hz), 8.29 (1H, d, J=2.4 Hz).

High performance liquid chromatography [manufactured by Nacalai Tesque Inc., COSMOSIL C₁₈ column (4.6 mm ID×150 mm), UV₂₈₀ nm detection, eluent: acetonitrile/water=3:1 (v/v), flow rate: 1.0 ml/min]: $t_R$=6.7 min.

Optical rotation [α]:(c 0.692, 1,4-dioxane): +92.6°.

| Elemental analysis for C₇₃H₉₀ClNO₄₅S: | | | |
|---|---|---|---|
| | C | H | N |
| Calculated (%): | 49.56 | 5.13 | 0.79 |
| Found (%): | 49.43 | 5.17 | 0.84 |

(3) Preparation of 2-chloro-4-nitrophenyl O-(2,3,4-tri-O-acetyl-6-deoxy-6-iodo-α-D-glucopyranosyl)-(1→4)-tris[O-(2,3,6-tri-O-acetyl-α-D-glucopyranosyl)-(1→4)]-2,3,6-tri-O-acetyl-β-D-glucopyranoside The procedure in the step (4) of Example 1 was repeated except that 2.00 g of 2-chloro-4-nitrophenyl O-(2,3,4-tri-O-acetyl-6-O-tosyl-α-D-glucopyranosyl)-(1→4)-tris[O-(2,3,6-tri-O-acetyl-α-D-glucopyranosyl)-(1→4)]-2,3,6-tri-O-acetyl-β-D-glucoyranoside (1.13 mmol) obtained in the step (2) of Example 3 was employed as the starting material to give 1.94 g of 2-chloro-4-nitrophenyl O-(2,3,4-tri-O-acetyl-6-deoxy-6-iodo-α-D-glucopyranoside)-(1→4)tris[O-(2,3,6-tri-O-acetyl-α-D-glucopyranosyl)-(1→4)]-2,3,6-tri-O-acetyl-β-D-glucopyranoside (1.13 mmol, yield 99.9%).

Melting point (°C.): 127.0–129.0.

UV-visible absorption spectrum: absorption maximum wavelength [λmax (CH₃CN)] (nm)=284 (log ε=4.10), 227 (sh), 214 (log=4.25).

IR spectrum (cm⁻¹): 3500, 2970, 1754, 1586, 1530, 1486, 1434, 1374, 1354, 1238, 1040, 946, 900.

NMR spectrum (200 MHz) ppm (CDCl₃) 1.99–2.19 (ca. 40H, each s), 3.13 (1H, dd, J=11.2 Hz, 6.2 Hz), 3.28 (1H, dd, J=11.2 Hz, 1.5 Hz), 3.68 (1H, ddd, J=8.8 Hz, 6.2 Hz, 1.5 Hz). 3.85–4.85 (m), 5.15–5.50 (m), 7.28 (1H, d, J=9.2 Hz), 8.16 (1H, dd, J=9.2 Hz, 2.8 Hz), 8.29 (1H, d, J=2.8 Hz).

High performance liquid chromatography [manufactured by Nacalai Tesque Inc., COSMOSIL C₁₈ column (4.6 mm ID×150 mm), UV₂₈₀ nm detection, eluent: acetonitrile/water=3:1 (v/v), flow rate: 1.0 ml/min]: $t_R$=6.0 min.

Optical rotation [α]: (c 0.634, 1,4-dioxane): +91.0°.

Elemental analysis for C₆₆H₈₃ClINO₄₂:

-continued

|  | C | H | N |
|---|---|---|---|
| Calculated (%): | 45.96 | 4.85 | 0.81 |
| Found (%): | 45.87 | 4.84 | 0.68 |

(4) Preparation of 2-chloro-4-nitrophenyl 6⁵-azido-6⁵-deoxy-β-D-maltopentaoside

The procedure in the step (6) of Example 1 was repeated with 2.04 g of the starting material 2-chloro-4-nitrophenyl pentadeca-O-acetyl-6⁵-azido-6⁵-deoxy-β-D-maltopentaoside (1.20 mmol, yield 95.2%) which was obtained by the same procedure as in the step (1) of Example 2 except that 2.16 g of 2-chloro-4-nitrophenyl O-(2,3,4-tri-O-acetyl-6-deoxy-6-iodo-α-D-glucopyranosyl)-(1→4)-tris[O-(2,3,6-tri-o-acetyl-α-D-glucopyranosyl)-(1→4)]-2,3,6-tri-O-acetyl-β-D-glucopyranoside (1.26 mmol) obtained in the step (3) of Example 3 was used as the starting material, to give 876 mg of the desired product 2-chloro-4-nitrophenyl 6⁵-azido-6⁵-deoxy-β-D-maltopentaoside (0.868 mmol, yield 72.3%).

Melting point (°C.): 130.0–135.5 (with decomposition).

UV-visible absorption spectrum: absorption maximum wavelength [λmax] (nm)=290 (log ε=3.98), 227 (log ε=3.99), 209 (log ε=4.20).

IR spectrum (cm¹): 3410, 2930, 2110, 1584, 1520, 1484, 1274, 1150, 1078, 1024.

NMR spectrum (200 MHz) ppm (DMSO-d₆) 3.05–3.90 (m), 4.20–4.55 (m), 4.74 (1H, br d, J=4.8 Hz), 4.96 (1H, br d, J=5.4 Hz), 5.05 (2H, d, J=3.7 Hz), 5.10 (2H, d, J=3.7 Hz), 5.25 (1H, d, J=7.6 Hz), 5.25–5.60 (m), 7.47 (1H, d, J=9.3 Hz), 8.19 (1H, dd, J=9.3 Hz, 2.7 Hz), 8.29 (1H, d, J=2.7 Hz).

High performance liquid chromatography [manufactured by Tosoh Corp., TSK gel Amide-80 column (4.6 mm ID×250 mm), UV₂₈₀ nm detection, eluent: acetonitrile/water=3:1 (v/v), flow rate: 1.0 ml/min]: t$_R$=6.7 min.

Optical rotation [α]:(c 0.516, H₂O): +92.4°.

| Elemental analysis for C₃₆H₅₃ClN₄O₂₇: | | | |
|---|---|---|---|
|  | C | H | N |
| Calculated (%): | 42.84 | 5.29 | 5.55 |
| Found (%): | 42.88 | 5.31 | 5.59 |

EXAMPLE 4

Preparation of 4-nitrophenyl 5⁷-eno-4⁷-O-methoxymethyl-α-D-maltoheptaoside (1) Preparation of 4-nitrophenyl O-(2,3-di-O-acetyl-α-D-glucopyranosyl)-(1→4)-pentakis[O-(2,3,6-tri-O-acetyl-α-D-glucopyranosyl)-(1→4)]-2,3,6-tri-O-acetyl-α-D-glucopyranoside A commercially available 4-nitropenyl α-D-maltoheptaoside in an amount of 15.0 g (11.8 mmol) was dissolved in 75 ml of anhydrous DMF, and 15.0 ml (113 mmol) of tetramethoxymethane and 7.5 g of Amberlyst (15E)$^{Trade\ Mark}$ were added to the solution. The mixture was subjected to reaction with stirring at 35° C. for 4 hours. Next, the reaction mixture was slowly dropped in 2.0 l of a 100 mM phosphate buffer (pH=7.0) under ice-cooling. The resulting mixture was purified by ODS (octadecylsilica gel) column chromatography, and the objective fraction eluted with an acetonitrile-water mixed solution (35:65 by volume) was concentrated. The procedure in the step (2) of Example 1 was repeated except that 10.0 g of the obtained oily 4-nitrophenyl 4⁷,6⁷-O-dimethoxymethylidene-α-D-maltoheptaoside (7.43 mmol, yield 63.0%) was used as the starting material to give 6.70 g of 4-nitrophenyl O-(2,3-di-O-acetyl-α-D-glucopyranosyl)-(1→4)-pentakis[O-(2,3,6-tri-O-acetyl-α-D-glucopyranosyl)-(1→4)]-2,3,6-tri-o-acetyl-α-D-glucoyranoside (3.17 mmol, two step total yield 42.6%).

UV-visible absorption spectrum: absorption maximum wavelength [λmax] (nm)=290 (log ε=3.98), 227 (sh), 209 (log ε=4.27).

IR spectrum (cm⁻¹): 3640, 2970, 1752, 1612, 1594, 1526, 1496, 1432, 1370, 1350, 1236, 1038, 948, 898.

NMR spectrum (200 MHz) ppm (CDCl₃) 2.00–2.20 (ca. 60H, each s), 3.65–4.85 (m), 5.15–5.55 (m), 7.08 (2H, d, J=9.1 Hz), 8.22 (2H, d, J=9.1 Hz).

High performance liquid chromatography [manufactured by Nacalai Tesque Inc., COSMOSIL C₁₈ column (4.6 mm ID×150 mm), UV₂₈₀ nm detection, eluent: acetonitrile/water=7:3 (v/v), flow rate: 1.0 ml/min]: t$_R$=5.3 min.

(2) Preparation of 4-nitrophenyl O-(2,3-di-O-acetyl-6-deoxy-6-iodo-4-O-methoxymethyl-α-D-glucopyranosyl)-(1→4)-pentakis[O-(2,3,6-tri-O-acetyl-α-D-glucopyranosyl)-(1→4)]-2,3,6-tri-O-acetyl-α-D-glucopyranoside The procedure in the step (1) of Example 3 was repeated except that 4-nitrophenyl O-(2,3-di-O-acetyl-α-D-glucopyranosyl)-(1→4)-pentakis[O-(2,3,6-tri-O-acetyl-α-D-glucopyranosyl)-(1→4)]-2,3,6-tri-o-acetyl-α-D-glucopyranoside (6.70 g, 3.17 mmol) obtained in the step (1) of Example 4 was used as the starting material to give 5.57 g of 4-nitrophenyl O-(2,3-di-O-acetyl-6-O-tosyl-α-D-glucopyranosyl)-(1→4)-pentakis[O-(2,3,6-tri-O-acetyl-α-D-glucopyranosyl)-(1→4)]-2,3,6-tri-O-acetyl-α-D-glucopyranoside (2.46 mmol, yield 77.6%). This tosyl derivative was dissolved in 40 ml of acetonitrile, and 1.93 g of methoxymethyl chloride (24 mmol) and 3.10 g of N,N-diisopropyl-N-ethylamine (24 mmol) were added to the solution. The mixture was subjected to reaction with stirring under reflux for 3 hours, and the solvent and the amine were removed by evaporation under reduced pressure. The residue was dissolved in 500 ml of methyl ethyl ketone, and 15.1 g of sodim iodide (100 mmol) was added to the solution. The mixture was subjected to reaction with stirring at 85° C. for 6 hours. The reaction mixture was then filtered through a Celite bed, and the methyl ethyl ketone contained in the filtrate was removed by evaporation under reduced pressure. The residue was purified by silica gel column chromatography, and the objective fraction eluted with an ethyl acetate-methanol-dichloromethane mixed solution (100:1:100 by volume) was concentrated to give 3.58 g of 4-nitrophenyl O-(2,3-di-O-acetyl-6-deoxy-6-iodo-4-O-methoxymethyl-α-D-glucopyranosyl)-(1→4)-pentakis[O-(2,3,6-tri-O-acetyl-α-D-glucoyranosyl)-(1→4)]-2,3,6-tri-O-acetyl-α-D-glucopyranoside (1.58 mmol, two-step total yield 64.2%) as an oily product.

UV-visible absorption spectrum: absorption maximum wavelength [λmax] (nm)=290 (log ε=3.98), 227 (sh), 209 (log ε=4.22).

IR spectrum (cm⁻¹): 3630, 2960, 1750, 1610, 1592, 1526, 1494, 1430, 1370, 1350, 1234, 1040, 960, 898.

NMR spectrum (200 MHz) ppm (CDCl$_3$) 2.00–2.19 (ca. 60H, each s), 3.22 (1H, dd, J=11.0 Hz, 6.5 Hz), 3.36 (3H, s), 3.46 (1H, dd, J=11.0 Hz, 1.5 Hz), 3.68 (1H, ddd, J=8.8 Hz, 6.5 Hz, 1.5 Hz), 3.85–4.85 (m), 5.15–5.50 (m), 7.08 (2H, d, J=9.0 Hz), 8.22 (2H, d, J =2.7 Hz).

High performance liquid chromatography [manufactured by Nacalai Tesque Inc., COSMOSIL C$_{18}$ column (4.6 mm ID×150 mm), UV$_{280}$ nm detection, eluent: acetonitrile/water=7:3 (v/v), flow rate: 1.0 ml/min]: t$_R$=10.8 min.

| Elemental analysis for C$_{90}$H$_{118}$INO$_{58}$: | | | |
|---|---|---|---|
| | C | H | N |
| Calculated (%): | 47.64 | 5.24 | 0.62 |
| Found (%): | 47.34 | 5.42 | 0.55 |

(3) Preparation of 4-nitrophenyl 5$^7$-eno-4$^7$-O-methoxymethyl-α-D-maltoheptaoside The procedures in the steps (5) and (6) of Example 1 were repeated except that 3.64 g of 4-nitrophenyl O-(2,3-di-O-acetyl-6-deoxy-6-iodo-4-O-methoxymethyl-α-D-glucopyranosyl)-(1→4)-pentakis[O-(2,3,6-tri-O-acetyl-α-D-glucopyranosyl)-(1→4)]-2,3,6-tri-O-acetyl-α-D-glucopyranoside (1.58 mmol) obtained in the step (2) of Example 4 was used as the starting material to give 1.15 g of 4-nitrophenyl 5$^7$-eno-4$^7$-O-methoxymethyl-α-D-maltoheptaoside (0.897 mmol, two-step total yield 56.8%).

UV-visible absorption spectrum: absorption maximum wavelength [λmax] (m)=289 (log ε=4.01), 228 (sh), 209 (log ε=4.25).

IR spectrum (cm$^{-1}$): 3410, 2930, 1644, 1612, 1592, 1520, 1500, 1346, 1250, 1152, 1080, 1020, 934, 876.

NMR spectrum (200 MHz) ppm (DMSO-d$_6$) 3.15–3.80 (m), 3.25 (3H, s), 4.25–4.60 (m), 4.56 (2H, d, J=2.0 Hz), 4.70–4.90 (m), 5.05 (2H, d, J=3.4 Hz), 5.11 (1H, d, J=3.7 Hz), 5.19 (3H, d, J=2.2 Hz), 5.23 (1H, d, J =3.4 Hz), 5.25–5.65 (m), 7.23 (2H, d, J=9.2 Hz), 8.23 (2H, d, J=9.2 Hz).

High performance liquid chromatography [manufactured by Tosoh Corp., TSK gel Amide-80 column (4.6 mm ID×250 mm), UV$_{280}$ nm detection, eluent: acetonitrile/water=65:35 (v/v), flow rate: 1.0 ml/min]: t$_R$=8.8 min.

| Elemental analysis for C$_{50}$H$_{77}$NO$_{37}$: | | | |
|---|---|---|---|
| | C | H | N |
| Calculated (%): | 46.77 | 6.04 | 1.09 |
| Found (%): | 46.50 | 6.28 | 1.01 |

EXAMPLE 5

Determination of α-amylase Activity (1)

(1) Preparation of a Substrate Solution

A substrate solution was prepared by dissolving 2-chloro-4-nitrophenyl 5$^5$-eno-4$^5$-O-mesyl-β-D-maltopentaoside (molecular weight: 1044) obtained in Example 1 in a 50 mM phosphate buffer (pH=7.0) containing 40 mM NaCl and 2 mM MgCl$_2$ to a concentration of 1.14 mM.

(2) Preparation of Coupled Enzyme Solution

Coupled enzyme solution was prepared by dissolving a commercially available α-glucosidase derived from yeast and a commercially available β-glucosidase derived from almond in a 50 mM phosphate buffer (pH=7.0) containing 40 mM NaCl and 2 mM MgCl$_2$ to a concentration of 117 units/ml and 13 units/ml, respectively. As the commercially available α- and β-glucosidases, those available from Toyobo Co., Ltd. were used.

(3) Preparation of Standard α-amylase Solutions

Standard α-amylase solutions were prepared by dissolving a commercially available human α-amylase (P:S=1:1) in purified water to a concentration of 0, 148, 284, 401 and 525 IU/l, respectively. As the commercially available human α-amylase, Calibzyme.AMY manufactured by International Reagents Corp. was employed. As for the activity of α-amylase, an amount of the enzyme which decomposes 1μ mol of (a commercially available) 2-chloro-4-nitrophenyl β-D-maltopentaoside at 37° C. for one minute was defined as 1 international unit (IU).

(4) Preparation of a Sample Solution

When a sample for determining α-amylase activity was liquid, it was used as a sample solution as it was. When it was solid, a sample solution was prepared by accurately weighing 500 mg of the sample and adding purified water to the sample so as the total volume to be 5 ml. If necessary, insoluble sunbstance in the sample solution was removed by the operations such as filtration before use.

(5) Preparation of a Calibration Curve

The coupled enzyme solution in an amount of 1.0 ml was added with stirring to 250 μl of a standard α-amylase solution, and the mixture was heated at 37° C. for 1 minute. Then, 2.0 ml of the substrate solution was added with stirring to the mixture, and the mixture was heated at 37° C. for 2 minutes before measuring the variation of absorbance at 400 nm for 2 minutes. A calibration curve was prepared on the basis of the relationship between the activities of standard α-amylase solutions and the variations of absorbance. As a result, the calibration curve is expressed by the equation:

$$U = 8.34 \cdot \Delta A \times 10^3 + 11.2$$

wherein
U: enzyme activity (IU/l), and
ΔA: variation of absorbance per minute.
The calibration curve is shown by a line graph in FIG. 1.

(6) Determination of α-amylase Activity in the Sample Solution

The coupled enzyme in an amount of 1.0 ml was added with stirring to 250 μl of the sample solution, and the mixture was heated at 37° C. for one minute. The substrate solution in an amount of 2.0 ml was added with stirring to the mixture, and the mixture was heated at 37° C. for 2 minutes before measuring the variation of the absorbance at 400 nm for 2 minutes. The activity of α-amylase in the sample solution can be determined by the calculation based on the measurements and the calibration curve prepared in the step (5). When the enzyme activity in the sample is beyond the application range (0–525 IU/l) of the calibration curve, the sample solution is diluted to a proper concentration with purified water before re-determination.

EXAMPLE 6

Determination of α-amylase Activity (2)

(1) Preparation of a Substrate Solution

A substrate solution was prepared by dissolving 2-chloro-4-nitrophenyl $6^5$-azido-$6^5$-deoxy-$\beta$-D-maltopentaoside (molecular weight: 1009) obtained in Example 3 in a 50 mM phosphate buffer (pH=7.0) containing 40 mM NaCl and 2 mM MgCl$_2$ to a concentration of 2.28 mM.

(2) Preparation of a Coupled Enzyme Solution (3) Preparation of Standard α-amylase Solutions (4) Preparation of a Sample Solution (5) Preparation of a Calibration Curve A coupled enzyme solution, standard α-amylase solutions, a sample solution and a calibration curve were prepared in the same procedures as in the step (2)–(5) of Example 5. As a result, the calibration curve is expressed by the equation:

$$U = 8.66 \cdot \Delta A \times 10^3 - 6.7$$

Figure 2:
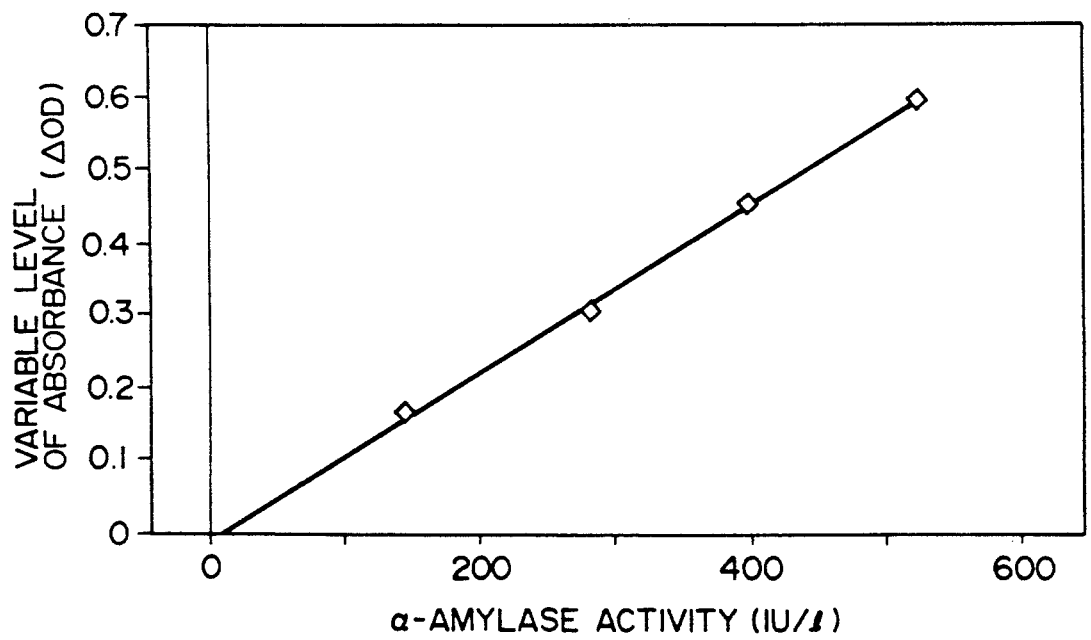
FIG. 2 is a graph which shows a calibration curve used for determining the activity of α-amylase in Example 6.

The calibration curve is shown by a line graph in FIG. 2.

(6) Determination of α-amylase Activity in the Sample Solution

The activity of α-amylase in a sample solution was determined in the same procedure as in the step (6) of Example 5.

EXAMPLE 7

The aforementioned $6^3$-azido-$6^3$-deoxymaltotrioside derivative and $6^5$-azido-$6^5$-deoxymaltopentaoside derivative which is the novel compound according to the present invention were compared for their hydrolysis rates with α-amylase.

(1) Preparation of 2-chloro-4-nitrophenyl $6^3$-azido-$6^3$-deoxy-$\beta$-D-maltotrioside 2-chloro-4-nitrophenyl $6^3$-azido-$6^3$-deoxy-$\beta$-D-maltotrioside was prepared in the same procedure as in Example 3 except that a commercially available 2-chloro-4-nitrophenyl $\beta$-D-maltotrioside (10.0 g, 15.2 mmoles) was employed as the starting material. The $6^3$-azido-$6^3$-deoxymaltotrioside was obtained in a yield of 1.14 g (1.67 mmol, eight-step total yield 11.0%) and had the following properties:

Melting point (°C.): 100.5–103.5 (with decomposition).

UV-visible absorption spectrum: absorption maximum wavelength [λmax] (nm)=290 (log $\epsilon$=3.99), 227 (log $\epsilon$=4.00), 209 (log $\epsilon$=4.22).

IR spectrum (cm$^{-1}$): 3410, 2940, 2112, 1586, 1522, 1486, 1274, 1156, 1078, 1024, 924, 896.

NMR spectrum (200 MHz) ppm (DMSO-d$_6$) 3.05–3.90 (m), 4.25–4.55 (m), 4.72 (1H, br d, J=5.0 Hz), 4.96 (1H, br d, J=5.5 Hz), 5.08 (1H, d, J=3.1 Hz), 5.11 (1H, d, J=3.8 Hz), 5.26 (1H, d, J=7.6 Hz), 5.25–5.60 (m), 7.48 (1H, d, J=9.2 Hz), 8.20 (1H, dd, J=9.2 Hz, 2.7 Hz), 8.30 (1H, d, J=2.7 Hz).

High performance liquid chromatography [manufactured by Tosoh Corp., TSK gel Amide-80 column (4.6 mm ID×250 mm), UV$_{280}$nm detection, eluent: acetonitrile/water=3:1 (v/v), flow rate: 1.0 ml/min]: $t_R$=3.9 min.

| Elemental analysis for $C_{24}H_{33}ClN_4O_{17}$: | | | |
|---|---|---|---|
| | C | H | N |
| Calculated (%): | 42.08 | 4.86 | 8.18 |
| Found (%): | 42.01 | 4.99 | 8.29/ |

(2) Preparation of Substrate Solution (a)

The substrate solution (a) was prepared by dissolving 2-chloro-4-nitorphenyl $6^5$-azido-$6^5$-deoxy-$\beta$-D-maltopentaoside (referred to hereinafter as the substrate of the present invention) obtained in Example 3 in a 50 mM phosphate buffer (pH=7.0) containing 40 mM NaCl and 2 mM MgCl$_2$ to a concentration of 3.00 mM.

(3) Preparation of Substrate Solution (b)

The substrate solution (b) was prepared by dissolving 2-chloro-4-nitrophenyl $6^3$-azido-$6^3$-deoxy-$\beta$-D-maltotrioside (referred to hereinafter as the reference substrate) obtained in the step (1) in a 50 mM phosphate buffer (pH=7.0) containing 40 mM NaCl and 2 mM MgCl$_2$ to a concentration of 3.00 mM.

(4) Preparation of a Coupled Enzyme Solution

A coupled enzyme solution was prepared in the same manner as in the step (2) of Example 5.

(5) Preparation of α-amylase Solutions

α-amylase solutions were prepared in the same manner as in the step (3) of Example 5 by dissolving a commercially available human α-amylase (P:S=1:1) in purified water to a concentration of 0, 250 and 500 IU/l, respectively.

(6) α-Amylase Hydrolysis

The coupled enzyme solution in an amount of 1.0 ml was added with stirring to 250 μl of the α-amylase solution, and the mixture was heated at 37° C. for one minute. Each of the substrate solution in an amount of 2.0 ml was added with stirring to the mixture, and the mixture was heated at 37° C. for 2 minutes before measuring the variation of the absorbance at 400 nm for 2 minutes. The result is shown in Table 1.

TABLE 1

| α-amylase activity (IU/l) | Increase in absorbance for 2 minutes (corrected by the 0 IU/l of α-amylase activity) | |
|---|---|---|
| | Substrate solution (a) (substrate solution of the present invention) | Substrate solution (b) (reference substrate solution) |
| 250 | 0.058 | 0.002 |
| 500 | 0.118 | 0.005 |

It is understood from Table 1 that the reference substrate is hardly hydrolyzed by α-amylase, whereas the substrate of the present invention is hydrolyzed satisfactorily by α-amylase.

EXAMPLE 8

The $5^3$-enomaltotrioside derivative and $5^5$-enomaltopentaoside derivative of the present invention were compared for their hydrolysis rates with α-amylase.

(1) Preparation of 2-chloro-4-nitrophenyl 5³-eno-4³-O-mesyl-β-D-maltotrioside The maltotrioside derivative was prepared in the same manner as in Example 1 except that a commercially available 2-chloro-4-nitrophenyl β-D-maltotrioside (10.0 g, 15.2 mmol) was employed as the starting material. The product was obtained in a yield of 1.23 g (1.71 mmol, seven-step total yield 11.3%) and had the following properties:

Melting point (°C.): 142.0–145.0 (with decomposition)

UV-visible absorption spectrum: absorption maximum wavelength [λmax] (nm)=289 (log ε=4.00), 228 (sh), 209 (log ε=4.44).

IR spectrum (cm$^{-1}$): 3400, 2920, 1642, 1584, 1518, 1488, 1348, 1276, 1250, 1152, 1080, 1020, 928, 892.

NMR spectrum (200 MHz) ppm (DMSO-$d_6$) 3.25–3.85 (m), 3.30 (3H, s), 4.04 (1H, br s), 4.30–4.60 (m), 4.58 (2H, br d, J=2.2 Hz), 5.11 (1H, d, J=3.8 Hz), 5.19 (1H, d, J=3.2 Hz), 5.26 (1H, d, J=7.4 Hz), 5.25–5.65 (m), 7.47 (1H, d, J=9.0 Hz), 8.18 (1H, dd, J=9.0 Hz, 2.7 Hz), 8.29 (1H, d, J=2.7 Hz).

High performance liquid chromatography [manufactured by Tosoh Corp., TSK gel Amide-80 column (4.6 mm ID×250 mm), UV$_{280}$ nm detection, eluent: acetonitrile/water=4:1 (v/v), flow rate: 1.0 ml/min]: $t_R$=4.6 min.

| Elemental analysis for $C_{25}H_{34}ClNO_{19}S$: | | | |
|---|---|---|---|
| | C | H | N |
| Calculated (%): | 41.70 | 4.76 | 1.95 |
| Found (%): | 41.53 | 4.88 | 1.90 |

(2) Preparation of Substrate Solution (a)

2-chloro-4-nitrophenyl 5⁵-eno-4⁵-O-mesyl-β-D-maltopentaoside (referred to hereinafter as substrate of the present invention) obtained in Example 1 was dissolved in a 50 mM phosphate buffer (pH=7.0) containing 40 mM NaCl and 2 mM MgCl$_2$ to a concentration of 3.00 mM.

(3) Preparation of Substrate Solution (b)

2-chloro-4-nitrophenyl 5³-eno-4³-O-mesyl-β-D-maltotrioside (referred to hereinafter as reference substrate) obtained in the previous step (1) was dissolved in a 50 mM phosphate buffer (pH=7.0) containing 40 mM NaCl an 2 mM MgCl$_2$ to a concentration of 3.00 mM.

(4) Preparation of a Coupled Enzyme Solution

A coupled enzyme solution was prepared in the same manner as in the step (2) of Example 5.

(5) Preparation of α-amylase Solutions

α-amylase solutions were prepared in the same manner as in the step (5) of Example 7.

(6) α-Amylase Hydrolysis

The variations of absorbance were measured in the same manner as in the step (6) of Example 7. The results are shown in Table 2.

TABLE 2

| | Increase in absorbance for 2 minutes (corrected by the O IU/1 of α-amylase activity) | |
|---|---|---|
| α-amylase activity (IU/l) | Substrate solution (a) (substrate solution of the present invention) | Substrate solution (b) (reference substrate solution) |
| 250 | 0.057 | 0.001 |
| 500 | 0.116 | 0.002 |

It is understood from Table 2 that the reference substrate is hardly hydrolyzed by α-amylase, whereas the substrate of the present invention is hydrolyzed extremely smoothly by α-amylase.

EXAMPLE 9

Coupled Enzyme Resistance Test (1)

(1) Preparation of Substrate Solution (a)

2-chloro-4-nitrophenyl 5⁵-eno-4⁵-O-mesyl-β-D-maltopentaoside (molecular weight: 1044; referred to hereinafter as substrate of the present invention) obtained in Example 1 was dissolved in a 50 mM phosphate buffer (pH=7.0) containing 40 mM NaCl and 2 mM MgCl$_2$ to a concentration of 3.0 mM.

(2) Preparation of Substrate Solution (b)

2-chloro-4-nitrophenyl β-D-maltopentaoside (molecular weight: 984; referred to hereinafter as reference substrate) obtained in the conventional method was dissolved in a 50 mM phosphate buffer (pH=7.0) containing 40 mM NaCl and 2 mM MgCl$_2$ to a concentation of 3.0 mM.

(3) Preparation of a Coupled Enzyme Solution

Coupled enzyme solution was prepared by dissolving a commercially available α-glucosidase derived from yeast and a commercially available β-glucosidase derived from almond in a 50 mM phosphate buffer (pH=7.0) containing 40 mM NaCl and 2 mM MgCl$_2$ to a concentration of 1053 units/ml and 15.5 units/ml, respectively. As the commercially available α- and β-glucosidases, those available from Toyobo Co., Ltd. were used.

(4) Coupled Enzyme Reaction

After 1.0 ml of a coupled enzyme solution was heated at 37° C. for 5 minutes, it was mixed sufficiently with 2.0 ml of the substrate solution of the present invention or the reference substrate solution and heated at 37° C. for 3 minutes. Then, variations of the absorbance at a wavelength of 400 nm were measured for 5 minutes.

Figure 3:
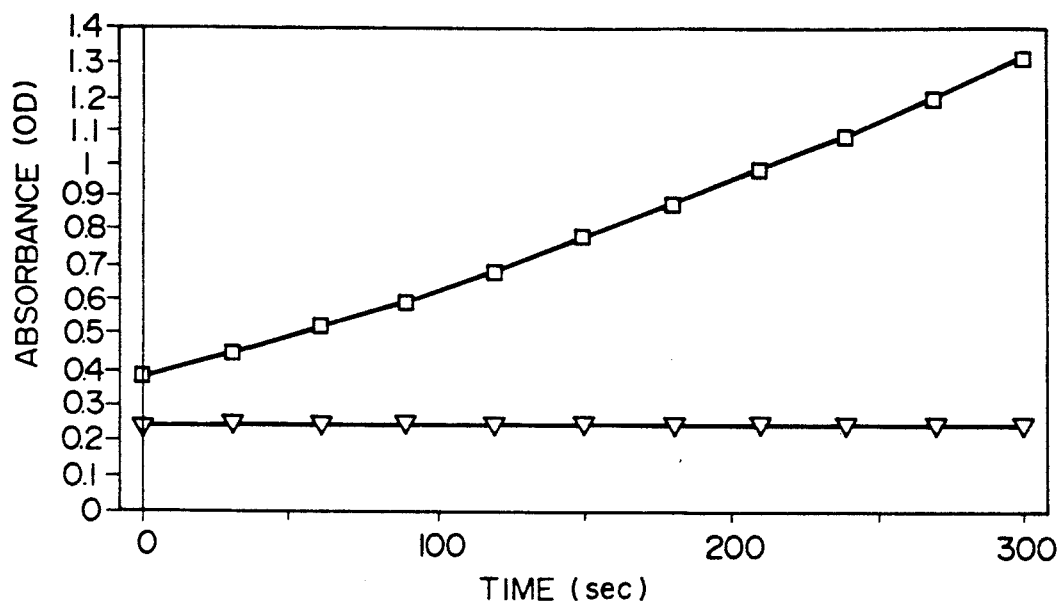
FIG. 3 is a graph which shows the stabilities of the substrate of the present invention and a reference substrate in a measurement system in Example 9.

The results are shown in FIG. 3. In FIG. 3, the marks ▽ show the plottings of the substrate solution (a) and the marks □ show the plottings of the substrate solution (b). It is understood from FIG. 3 that the substrate of the present invention is not hydrolyzed by the coupled enzyme and is stable in a measuring system.

EXAMPLE 10

Coupled Enzyme Resistance Test (2)

Figure 4:
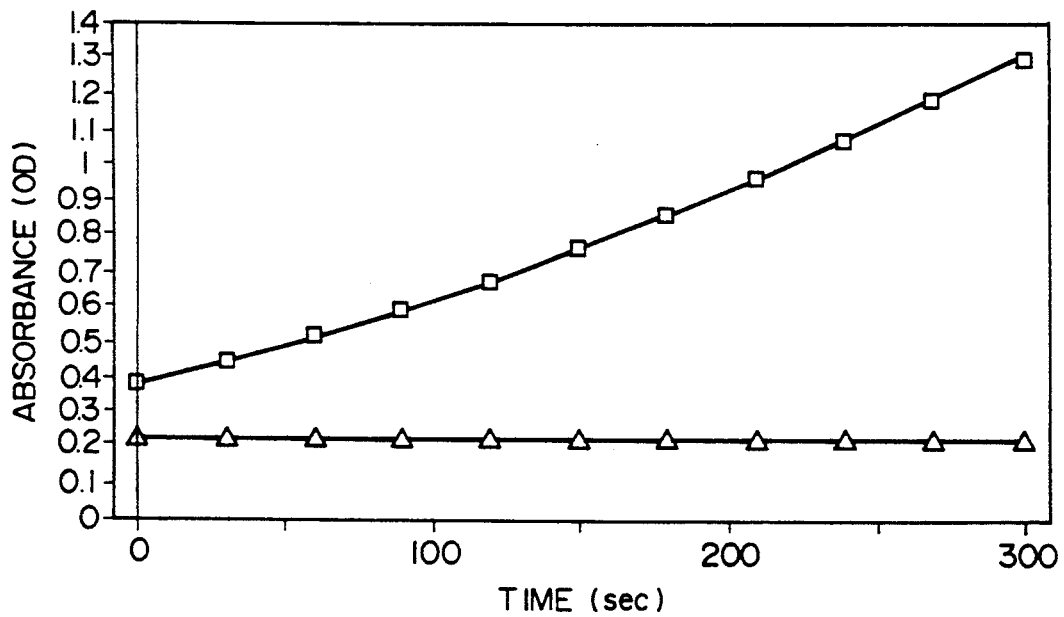
FIG. 4 is a graph which shows the stabilities of the substrate of the present invention and a reference substrate in a measurement system in Example 10.

The test was carried out in the same manner as in Example 9 except that 2-chloro-4-nitrophenyl 6⁵-azido-6⁵-deoxy-β-D-maltopentaoside (molecular weight: 1009; referred to hereinafter as the substrate of the present invention) obtained in Example 3 was employed as the substrate (a). The results are shown in FIG. 4. In FIG. 4, marks Δ show the plottings of the substrate solution (a) and the marks □ show the plottings of the substrate solution (b). It is understood from FIG. 4 that the substrate of the present invention is not hydrolyzed by the coupled enzyme and is stable in a measuring system.

EXAMPLE 11

Reagents for Determination (1)

(1) Preparation of Reagents

Reagents were prepared by dissolving the following ingredients in a certain concentration in purified water.

| Ingredients | Concentration |
| --- | --- |
| 2-chloro-4-nitrophenyl $5^5$-eno-$4^5$-O-mesyl-$\beta$-D-maltopentaoside | 0.70 mM |
| $\alpha$-glucosidase | 40 units/ml |
| $\beta$-glucosidase | 5.0 units/ml |
| $\beta$-glycerophosphate buffer (pH = 7.0) | 20 mM |
| bovine serum albumin | 0.05% |

(2) Determining Procedure

When a sample to be determined is liquid, it is used directly as a sample solution. When a sample is solid, a sample solution was prepared by accurately weighing 500 mg of the sample and adding purified water to the sample so as the total volume to be 5 ml. The reagent (3.0 ml) preliminarily heated at 37° C. for two minutes was added with stirring to 250 μl of the sample solution, and the mixture was heated at 37° C. for two minutes to measure the variation of the abosrbance at 400 nm for 2 minutes. The activity of $\alpha$-amylase in the sample solution can be determined by calculation based on the measurements and the calibration curve prepared preliminarily. When the enzyme activity in the sample is beyond the application range (0–525 IU/l) of the calibration curve, the sample solution is diluted to a proper concentration with purified water before re-determination.

EXAMPLE 12

Reagents for Determination (2)

Preparation of Reagents and Determining Procedure

Procedures in Example 11 was repeated except that 2-chloro-4-nitrophenyl $5^5$-eno-$4^5$-O-mesyl-$\beta$-D-maltopentaoside was replaced with 2-chloro-4-nitrophenyl $6^5$-azido-$6^5$-deoxy-$\beta$-D-maltopentaoside and used in a concentration of 2.00 mM.

EXPERIMENTAL EXAMPLE

Km values, hydrolysis rate, water solubility and the patterns of action in the hydrolysis of the present substrates 2-chloro-4-nitrophenyl $5^5$-eno-$4^5$-O-mesyl-$\beta$-D-maltopentaoside (EMG5CNP) and 2-chloro-4-nitrophenyl $6^5$-azido-$6^5$-deoxy-$\beta$-D-maltopentaoside (ADG5CNP) obtained in Example were examined in accordance with the following methods. The results are shown in Tables 3 and 4.

As the reference substrate, a commercially available 2-chloro-4-nitrophenyl $\beta$-D-maltopentaoside (G5CNP) was used.

(1) Km Value (i) Preparation of Substrate Solution (a)

Substrate solutions were prepared by dissolving in a 50 mM phosphate buffer (pH=7.0) containing 40 mM NaCl and 2 mM MgCl$_2$ a substrate to 0.16, 0.32, 0.48, 0.64, 0.80 and 0.96 mM, respectively.

(ii) Rough Calculation of Km Value

The Km value of each substrate solution was obtained by measuring the hydrolysis rate of the substrate in accordance with the same procedure as in the measurement of hydrolysis rate described below and roughly calculating the Lineweaver-Burk's reciprocal plot (see "Tanpaku-Kohso no Jikken-hou", ed. Takeichi Horio & Jinpei Yamashita, Nanko-do, 1981).

(iii) Preparation of Substrate Solution (b)

Each substrate was dissolved in a 50 mM phosphate buffer (pH=7.0) containing 40 mM NaCl and 2 mM MgCl$_2$ to make three substrate solutions in a concentration of 0.8–1.6 times and three substrate solutions in a concentration of 1.6–3.2 times per the roughly calculated Km value in the aforementioned paragraph (ii).

(iv) Measurement of Km Value

The Km value was calculated in accordance with the same procedure as in the aforementioned paragraph (ii).

(2) Hydrolysis Rate (i) Preparation of Substrate Solutions

Each substrate was dissolved in a 50 mM phosphate buffer (pH=7.0) containing 40 mM NaCl and 2 mM MgCl$_2$ so that the substrate solution had a concentration of 7–9 times to the Km value. The concentration corresponds to approximately five times of the Km value to human $\alpha$-amylase in the reaction with $\alpha$-amylase described below, and thus the substrate solution has a sufficient amount of the substrate to reach the maximum reaction rate.

(ii) Preparation of Coupled Enzyme Solution

The coupled enzyme solution was prepared in the same manner as in the step (2) of Example 5.

(iii) Preparation of $\alpha$-amylase Solutions

Commercially available human P type and S type $\alpha$-amylase solutions having a concentration of ca. 500 IU/l were prepared in the same manner as in the step (3) of Example 5.

(iv) Determination of Hydrolysis Rate ($\alpha$-amylase Reaction)

With 250 μl of the $\alpha$-amylase solution prepared in (iii) was mixed 1.0 ml of the coupled enzyme. The mixture was heated at 37° C. for 1 minute, and 2.0 ml of the substrate solution was added with stirring to the mixture. The variation of absorbance at 400 nm was measured for 2 minutes after heating the mixture at 37° C. for 2 minutes. The hydrolysis rate of each substrate, namely the variable absorbance per unit time was expressed with the relative values to the hydrolysis rate of 3 mM G5CNP (the reference substrate) which is defined as 10.

(3) Solubility in Water

To 100 ml of water was added 20 g of a substrate, and the dissolution state was observed.

(4) Patterns of Action

Each substrate was dissolved in a 50 mM phosphate buffer (pH=7.0) containing 40 mM NaCl and 2 mM $MgCl_2$ so that the substrate solution had a concentration of 0.5 mM. To 1.0 ml of the substrate solution was added 100 μl of the α-amylase solution prepared in the paragraph (iii) of the aforementioned hydrolysis rate, and the mixture, after stirred sufficiently, was subjected to reaction at 37° C. for 20 minutes. The hydrolyzed product was determined quantitatively by the high performance liquid chromatography of the reaction mixture.

TABLE 3

| Substrate | Am | Km value (mM) | Hydrolysis rate | Solubility in water |
|---|---|---|---|---|
| EMG5CNP | P | 0.13 | 10 | Good |
|  | S | 0.14 | 10 |  |
| ADG5CNP | P | 0.17 | 10 | Good |
|  | S | 0.26 | 10 |  |
| G5CNP | P | 0.29 | 10 | Good |
|  | S | 0.37 | 10 |  |

TABLE 4

| Substrate | Am | Patterns of action [Hydrolyzed product (mol %)] | | | |
|---|---|---|---|---|---|
|  |  | G4CNP | G3CNP | G2CNP | GCNP |
| EMG5CNP | P | 0 | 0 | 97 | 3 |
|  | S | 0 | 0 | 97 | 3 |
| ADG5CNP | P | 0 | 3 | 97 | 0 |
|  | S | 0 | 0 | 100 | 0 |
| G5CNP | P | 8 | 8 | 81 | 3 |
|  | S | 4 | 11 | 83 | 2 |

Note
Am: Two human α-amylases (isozymes),
P: α-amylase derived from human pancreatic juice,
S: α-amylase derived from human saliva.

It is understood from Tables 3 and 4 that the substrates of the present invention is hydrolyzed at essentially single D-glucosidic linkage, and the patterns of action and hydrolysis rate with the two α-amylases are equal, and that they have high affinity to α-amylase and good hydrolysis rate and solubility in water, so that they are very excellent as the substrate for the determination of the α-amylase activity.

What is claimed is:

1. A maltooligoside derivative represented by the formula:

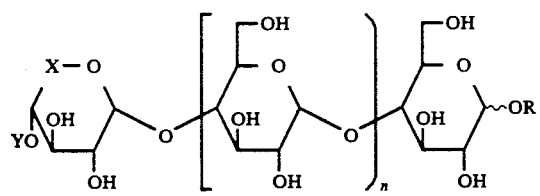

wherein n denotes an integer of 3-5, R represents an aromatic chromophoric group, X represents a group >CHCH₂N₃ or >C=CH₂, and Y represents a hydrogen atom, a substituted or unsubstituted hydrocarbon group, or alkyl- or arylsulfonyl group.

2. A maltooligoside derivative according to claim 1, wherein the aromatic chromophoric group R is represented by the formulae:

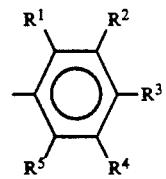

wherein $R^1$-$R^5$, which may be the same or different, represent a hydrogen atom, a halogen atom, a nitro group, an alkyl group, an aryl group, an aralkyl group, an amino group, a sulfonic acid group or a carboxyl group, or $R^1$ and $R^2$ or $R^2$ and $R^3$ may be bonded together to form a fused aromatic ring, wherein $R^6$ represents a hydrogen atom or an alkyl group, wherein $R^7$ represents a hydrogen atom or a halogen atom, wherein $R^8$-$R^{15}$, which may be the same or different, represent a hydrogen atom, a halogen atom, a nitro group, an alkyl group, an aryl group, an aralkyl group, an amino group, a sulfonic acid group or a carboxyl group, $R^8$ and $R^9$ or $R^{10}$ and $R^{11}$ may be bonded together to form a fused aromatic ring, $R^9$ and $R^{10}$ and/or $R^{13}$ and $R^{14}$ may represent a common oxygen atom, respectively, to form a fused ether ring, and Z represents a nitrogen atom or N→O.

3. A maltopentaoside derivative according to claim 1, which is 2-chloro-4-nitrophenyl 6⁵-azido-6⁵-deoxy-D-maltopentaoside, 2-chloro-4-nitrophenyl 6⁵-azido-6⁵-deoxy-4⁵-O-mesyl-D-maltopentaoside, 2-chloro-4-nitrophenyl 5⁵-eno-D-maltopentaoside, 2-chloro-4-nitrophenyl 5⁵-eno-4⁵-O-mesyl-D-maltopentaoside, 4-nitrophenyl 5⁵-eno-4⁷-O-methoxymethyl-D-maltopentaoside, 4-nitrophenyl 6⁷-azido-6⁷-deoxy-D-maltoheptaoside, 2,4-dichlorophenyl 6⁷-azido-6⁷-deoxy-4⁷-O-tosyl-D-maltoheptaoside, phenolindo-3'-chlorophenyl 6⁵-azido-6⁵-deoxy-4⁵-O-methyl-D-maltopentaoside, 4-methylumbelliferonyl 6⁵-azido-6⁵-deoxy-D-maltopentaoside, resazurinyl $5^6$-eno-D-maltohexaoside, luciferinyl $6^7$-azido-$6^7$-deoxy-$4^7$-O-allyl-D-maltoheptaoside or phenolindo-3'-chlorophenyl $5^5$-eno-$4^5$-O-(2-methoxy)ethoxymethyl-D-maltopentaoside.

4. A maltopentaoside derivative according to claim 3, which is 2-chloro-4-nitrophenyl $6^5$-azido-$6^5$-deoxy-D-maltopentaoside or 2-chloro-4-nitrophenyl $5^5$-eno-$4^5$-O-mesyl-D-maltopentaoside.

5. A reagent for determining α-amylase activity comprising the maltooligoside derivative according to claim 1 as an effective ingredient and a carrier material therefor.

6. A process for determining α-amylase activity, which comprises adding an α-anomer of the maltooligoside derivative according to claim 1 and α-glucosidase and/or glucoamylase to an α-amylase containing sample to conduct an enzymatic reaction and quantitatively determining a liberated aromatic chromophoric compound.

7. A process for determining α-amylase activity, which comprises adding a β-anomer of the maltooligoside derivative according to claim 1 or a mixture of an α-anomer and β-anomer thereof, α-glucosidase and/or glucoamylase and β-glucosidase to an α-amylase containing sample to conduct an enzymatic reaction and quantitatively determining a liberated aromatic chromophoric compound.

* * * * *